(12) United States Patent
Altschuler

(10) Patent No.: US 9,770,531 B2
(45) Date of Patent: Sep. 26, 2017

(54) SOLID SUBSTRATES FOR MITIGATING OR PREVENTING CELL AND TISSUE ADHESION AND VASCULARIZATION

(71) Applicant: CARTIHEAL (2009) LTD., Kfar Saba (IL)

(72) Inventor: Nir Altschuler, Tsur Yitskhak (IL)

(73) Assignee: CARTIHEAL (2009) LTD, Kfar Saba (IL)

( * ) Notice: Subject to any disclaimer, the term of this patent is extended or adjusted under 35 U.S.C. 154(b) by 93 days.

(21) Appl. No.: 14/767,432

(22) PCT Filed: Feb. 10, 2014

(86) PCT No.: PCT/IL2014/050140
§ 371 (c)(1),
(2) Date: Aug. 12, 2015

(87) PCT Pub. No.: WO2014/125477
PCT Pub. Date: Aug. 21, 2014

(65) Prior Publication Data
US 2015/0374880 A1    Dec. 31, 2015

Related U.S. Application Data

(60) Provisional application No. 61/763,981, filed on Feb. 13, 2013, provisional application No. 61/763,985, (Continued)

(51) Int. Cl.
| | | |
|---|---|---|
| A61K 36/00 | (2006.01) |
| A61L 27/36 | (2006.01) |
| A61L 27/52 | (2006.01) |
| A61L 27/54 | (2006.01) |
| A61L 27/56 | (2006.01) |
| A61L 27/12 | (2006.01) |
| A61L 27/20 | (2006.01) |
| A61L 27/40 | (2006.01) |
| C01B 25/32 | (2006.01) |
| C01F 11/18 | (2006.01) |
| G01N 1/00 | (2006.01) |
| A61L 27/50 | (2006.01) |
| A61F 2/28 | (2006.01) |
(Continued)

(52) U.S. Cl.
CPC ............ A61L 27/3608 (2013.01); A61F 2/28 (2013.01); A61F 2/30 (2013.01); A61F 2/30756 (2013.01); A61L 27/12 (2013.01); A61L 27/20 (2013.01); A61L 27/3604 (2013.01); A61L 27/365 (2013.01); A61L 27/3637 (2013.01); A61L 27/3654 (2013.01); A61L 27/3834 (2013.01); A61L 27/40 (2013.01); A61L 27/50 (2013.01); A61L 27/52 (2013.01); A61L 27/54 (2013.01); A61L 27/56 (2013.01); C01B 25/32 (2013.01); C01F 11/18 (2013.01); G01N 1/00 (2013.01); *A61F 2230/0006* (2013.01); *A61F 2230/0065* (2013.01); *A61F 2230/0067* (2013.01); *A61F 2230/0069* (2013.01); *A61F 2230/0071* (2013.01); *A61F 2230/0086* (2013.01); *A61L 2300/112* (2013.01); *A61L 2300/41* (2013.01); *A61L 2300/412* (2013.01); *A61L 2300/414* (2013.01); *A61L 2300/426* (2013.01); *A61L 2430/02* (2013.01); *A61L 2430/06* (2013.01); *C01P 2006/90* (2013.01)

(58) Field of Classification Search
None
See application file for complete search history.

(56) References Cited

U.S. PATENT DOCUMENTS

| 8,790,681 B2 | 7/2014 | Altschuler et al. |
| 8,808,725 B2 | 8/2014 | Altschuler et al. |
| 8,932,581 B2 | 1/2015 | Vago |

FOREIGN PATENT DOCUMENTS

| CN | 1386478 A * | 12/2002 |
| WO | WO 2009/066283 A2 | 5/2009 |

(Continued)

OTHER PUBLICATIONS

International Search Report (ISR) for PCT/IL2014/050140; I.A. fd Feb. 10, 2014, mailed May 23, 2014 from the European Patent Office, Rijswijk, Netherlands.
(Continued)

*Primary Examiner* — Qiuwen Mi
(74) *Attorney, Agent, or Firm* — Sterne, Kessler, Goldstein & Fox P.L.L.C.

(57) ABSTRACT

This invention provides solid substrates for mitigating or preventing cell or tissue adherence and/or vascularization, which solid substrates comprise a marine organism skeletal derivative and are characterized by a specific fluid uptake capacity value of less than 40%, processes for selection of the same and applications of the same. This invention also provides solid substrates for mitigating or preventing cell or tissue adherence and/or vascularization, which solid substrates are characterized by having a contact angle value of more than 60 degrees, when in contact with a fluid. This invention also provides solid substrates for mitigating or preventing cell or tissue adherence and/or vascularization, which solid substrate is characterized by a minimal surface roughness (Ra) or substantial surface smoothness, as measured by scanning electron microscopy or atomic force microscopy. The invention also provides processes for selection of an optimized coral-based solid substrate.

20 Claims, 12 Drawing Sheets

Related U.S. Application Data filed on Feb. 13, 2013, provisional application No. 61/764,467, filed on Feb. 13, 2013, provisional application No. 61/764,496, filed on Feb. 13, 2013, provisional application No. 61/773,219, filed on Mar. 6, 2013, provisional application No. 61/773,228, filed on Mar. 6, 2013.

(51) Int. Cl.
*A61F 2/30* (2006.01)
*A61L 27/38* (2006.01)

(56) References Cited

FOREIGN PATENT DOCUMENTS

| WO | WO 2010/058400 A1 | 5/2010 |
|---|---|---|
| WO | WO 2010/146575 A2 | 12/2010 |
| WO | WO 2014/125478 A1 | 8/2014 |

OTHER PUBLICATIONS

International Preliminary Report on Patentability (Chapter II of the Patent Cooperation Treaty) for PCT/IL2014/050140; I.A. fd Feb. 10, 2014, completed May 12, 2015, by the European Patent Office, Rijswijk, Netherlands.

Vago, R. et al., "Hard tissue remodeling using biofabricated coralline biomaterials," J Biochem Biophys Methods 50(2-3):253-259 (Jan. 2002), Elsevier/North-Holland Biomedical Press, Amsterdam, Netherlands.

Xu, Y. et al., "Hydrothermal conversion of coral into hydroxyapatite," Materials Characterization 47:83-87 (Aug. 2001), Elsevier, Amsterdam, Netherlands.

Ben-Nissan, B. et al., "Morphology of sol-gel derived nano-coated coralline hydroxyapatite," Biomaterials 25(20):4971-4975 (Sep. 2004), Elsevier Science Publishers BV, Amsterdam, Netherlands.

\* cited by examiner

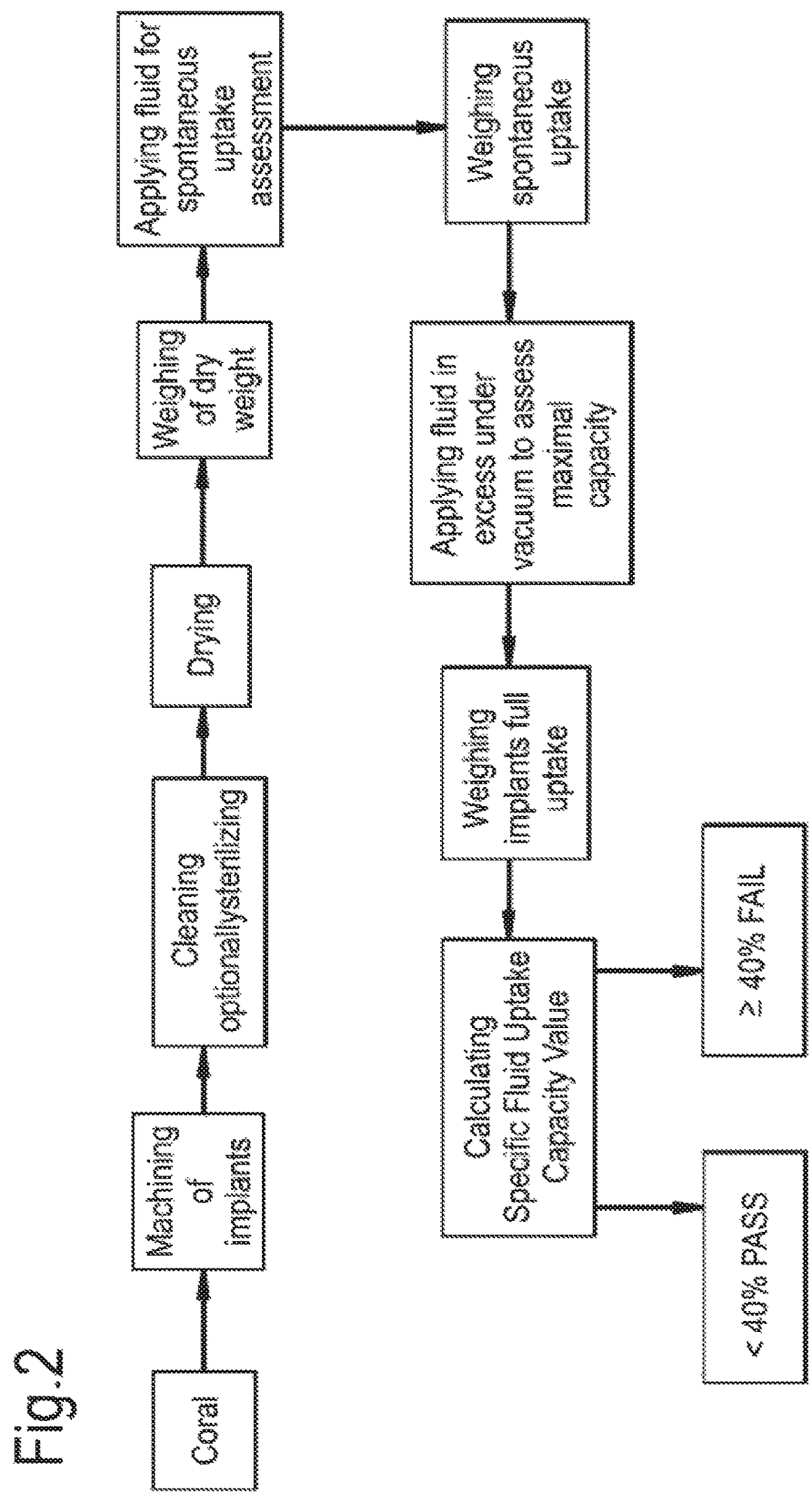

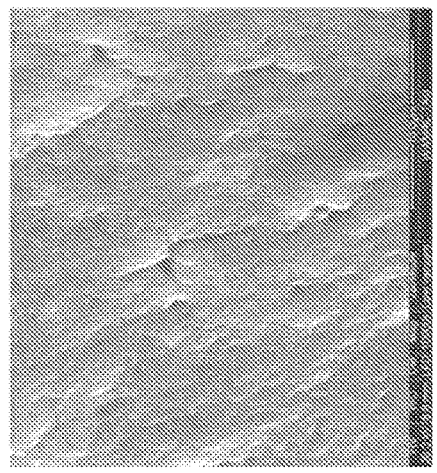
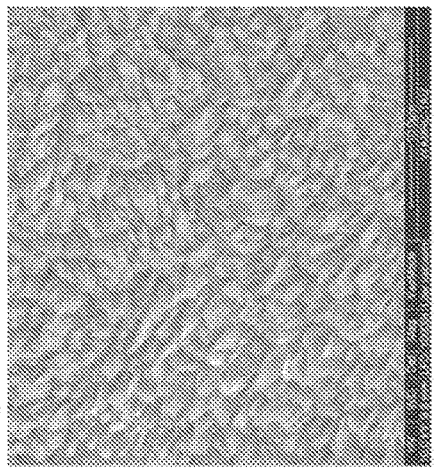
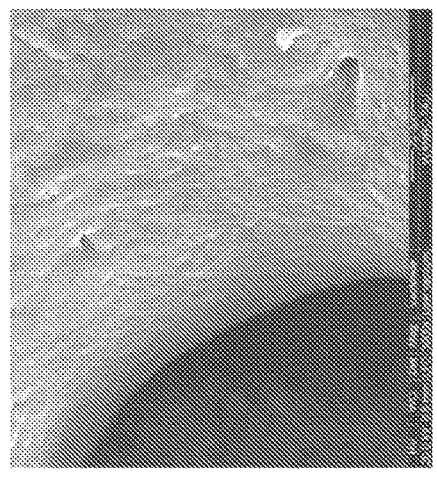
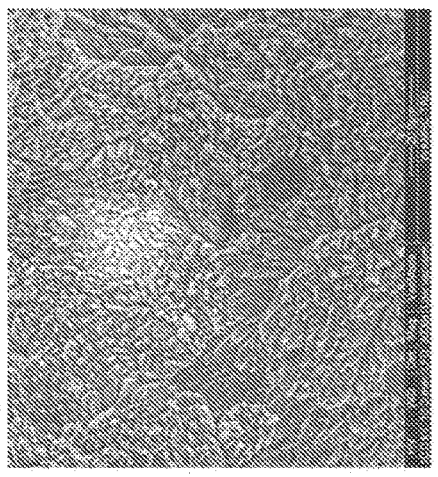
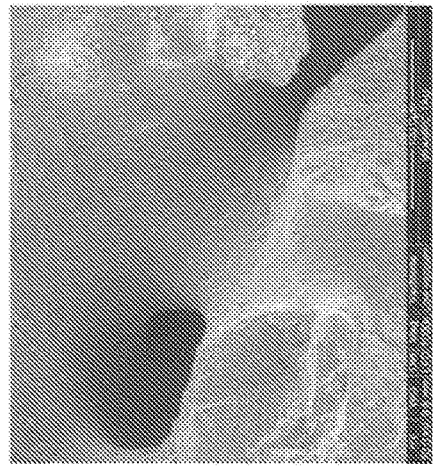
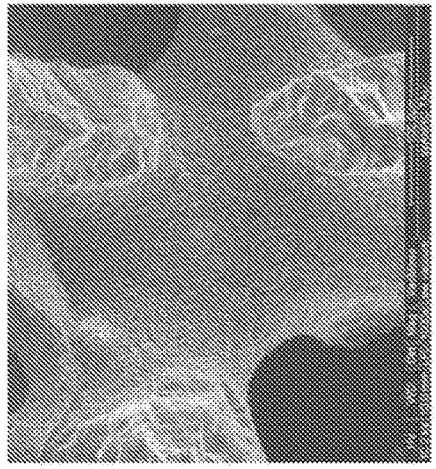

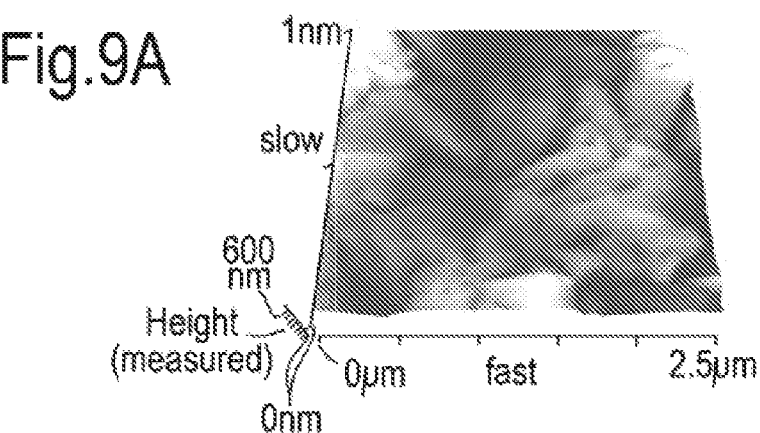
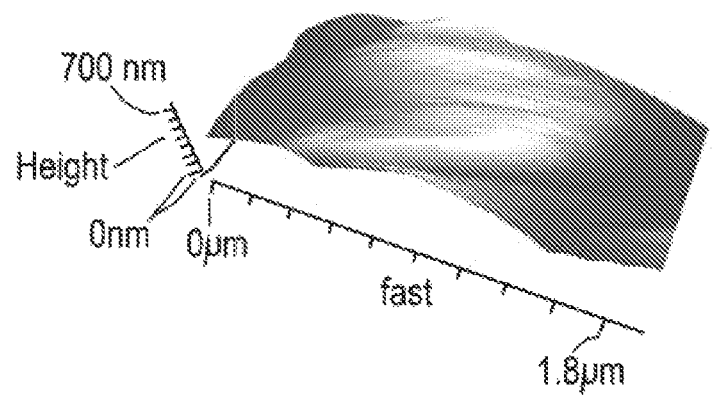
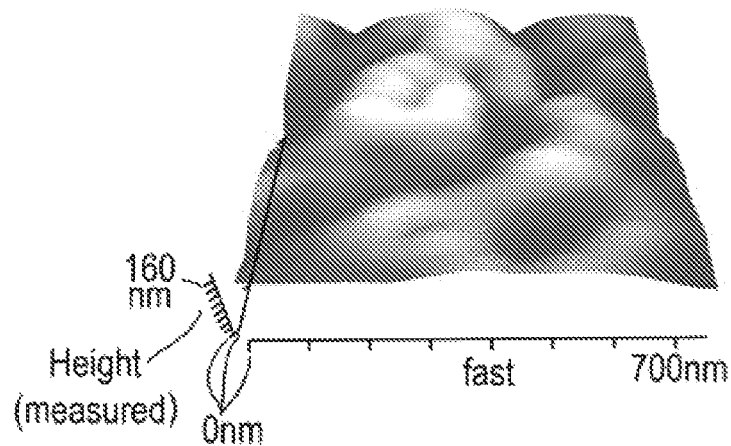

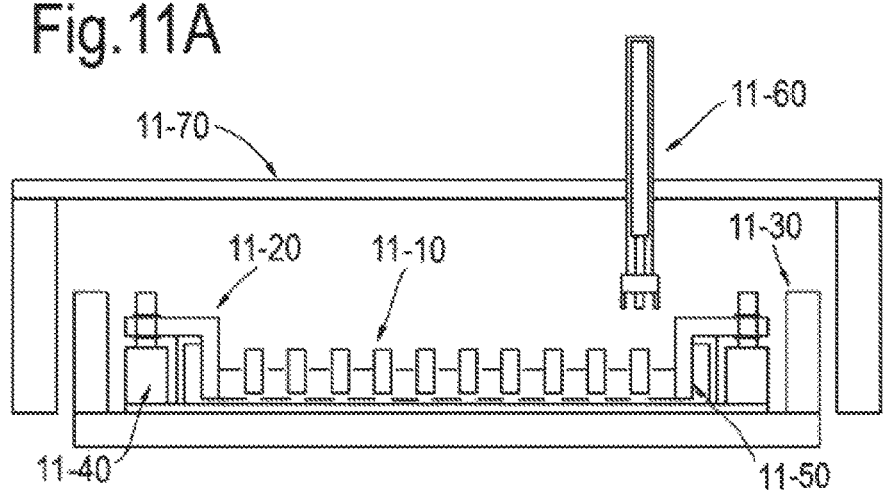
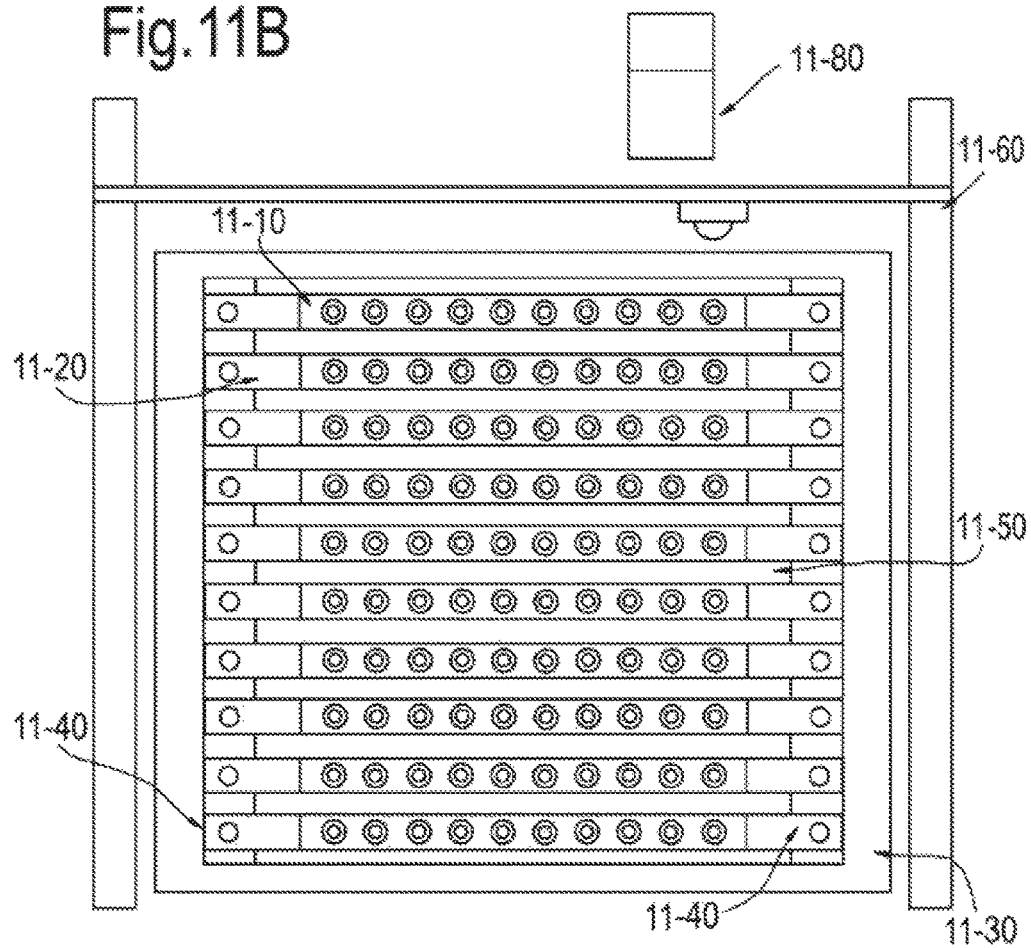

SOLID SUBSTRATES FOR MITIGATING OR PREVENTING CELL AND TISSUE ADHESION AND VASCULARIZATION

CROSS REFERENCE TO RELATED APPLICATIONS

This application claims the benefit of U.S. Provisional Application Ser. No. 61/763,981, U.S. Provisional Application Ser. No. 61/763,985, U.S. Provisional Application Ser. No. 61/764,467, and U.S. Provisional Application Ser. No. 61/764,496, all of which were filed Feb. 13, 2013, as well as claiming the benefit to U.S. Provisional Application Ser. No. 61/773,219 and U.S. Provisional Application Ser. No. 61/773,228, both of which were filed Mar. 6, 2013, all of which are hereby incorporated by reference herein in their entirety.

BACKGROUND OF THE INVENTION

In many disease states, the body lacks or loses control over angiogenesis and its ability to regulate or limit vascularization. Excessive angiogenesis and subsequent vascularization occurs in diseases such as cancer, macular degeneration, diabetic retinopathy, arthritis and psoriasis. In these conditions, new blood vessels feed diseased tissues destroy normal tissues, and in the case of cancer, the new vessels allow tumor cells to escape into the circulation and lodge in other organs (tumor metastasis).

Expansion of tumor volume beyond a certain phase requires the induction of new capillary blood vessels. For example, pulmonary micrometastases in the early pre-vascular phase in mice would be undetectable except by high power microscopy on histological sections. Further indirect evidence supporting the concept that tumor growth is angiogenesis dependent is found in U.S. Pat. Nos. 5,639,725, 5,629,327, 5,792,845, 5,733,876, and 5,854,205.

Neovascularization in the eye is the basis of severe ocular diseases such as age-related macular degeneration (AMID) and Diabetic retinopathy. AMD is the most common cause of legal, irreversible blindness in patients aged 65 and over in the US, Canada, England, Wales, Scotland and Australia. Although the average age of patients when they lose central vision in their first eye is about 65 years, some patients develop evidence of the disease in their fourth or fifth decade of life. Approximately 10% to 15% of patients manifest the exudative (wet) form of the disease. Exudative AMD is characterized by angiogenesis and the formation of pathological neo-vasculature. The disease is bilateral with accumulating chances of approximately 10% to 15% per annum of developing the blinding disorder in the fellow eye.

Diabetic retinopathy is a complication of diabetes that occurs in approximately 40 to 45 percent of those diagnosed with either Type I or Type II diabetes. Diabetic retinopathy usually affects both eyes and progresses over four stages. The first stage, mild non-proliferative retinopathy, is characterized by micro-aneurysms in the eye. Small areas of swelling in the capillaries and small blood vessels of the retina occurs. In the second stage, moderate non-proliferative retinopathy, the blood vessels that supply the retina become blocked. In severe non-proliferative retinopathy, the third stage, the obstructed blood vessels lead to a decrease in the blood supply to the retina, and the retina signals the eye to develop new blood vessels (angiogenesis) to provide the retina with blood supply. In the fourth and most advanced stage, proliferative retinopathy, angiogenesis occurs, but the new blood vessels are abnormal and fragile and grow along the surface of the retina and vitreous gel that fills the eye. When these thin blood vessels rupture or leak blood, severe vision loss or blindness can result.

There is a need for the discovery and development of additional anti-angiogenic agents that may be used alone, or in combination with known angiogenic agents, in order to treat or prevent angiogenesis-related disorders.

Many diseases and conditions whose treatment is sought would benefit from the ability to mitigate cell or tissue adhesion or vascularization within a desired site in a body of a subject.

SUMMARY OF THE INVENTION

In some embodiments, the present invention provides solid substrates for mitigating cell or tissue adhesion or vascularization. In some embodiments, the invention provides a process for the selection of an optimized marine organism skeletal derivative-based solid substrate for mitigating cell or tissue adhesion or vascularization, comprising establishing a specific fluid uptake capacity value for the marine organism skeletal derivative-based solid material, and selecting a marine organism skeletal derivative-based solid material characterized by a specific fluid uptake capacity value of less than 40%.

In one embodiment, the invention provides a process for selection of an optimized marine organism skeletal derivative-based solid substrate for mitigating or preventing cell or tissue adhesion or vascularization, said process comprising:
  isolating a marine organism skeletal derivative-based solid material;
  establishing a specific fluid uptake capacity value of said marine land or marine organism skeletal derivative-based solid material, which specific fluid uptake capacity value is determined by establishing a spontaneous fluid uptake value divided by a total fluid uptake value; or
  contacting said marine organism skeletal derivative-based solid material with a fluid and establishing a contact angle for said marine organism skeletal derivative; and
  selecting a marine organism skeletal derivative-based solid material characterized by a specific fluid uptake capacity value of less than 40%; or
  selecting a marine organism skeletal derivative-based solid material characterized by a contact angle of more than 60 degrees.

In some embodiments, the invention provides a solid substrate for mitigating cell or tissue adhesion or vascularization, which solid substrate comprises a marine organism skeletal derivative and is characterized by a specific fluid uptake capacity value of less than 40%, which specific fluid uptake capacity value is determined by establishing a spontaneous fluid uptake value divided by a total fluid uptake value or wherein said solid substrate is characterized by having a contact angle value of more than 60 degrees, when in contact with a fluid.

In some embodiments, the solid substrate is characterized by a specific fluid uptake capacity value of less than 45%, and in some embodiments, the solid substrate is characterized by a specific fluid uptake capacity value of less than 40%, and in some embodiments, the solid substrate is characterized by a specific fluid uptake capacity value of less than 35%, and in some embodiments, the solid substrate is characterized by a specific fluid uptake capacity value of less than 30%, and in some embodiments, the solid substrate is characterized by a specific fluid uptake capacity value of less than 20%. In some embodiments, the solid substrate is characterized by a specific fluid uptake capacity value of less than from 1-40%.

In some embodiments, the term "a specific fluid uptake capacity value" is also referred to herein as "SFUC" or "SWC", all of which are to be understood as to be interchangeable.

In some embodiments, a specific fluid uptake capacity value of this invention is determined using an apparatus, which is automated. In some aspects, and as exemplified and further described hereinunder, assessment of the specific fluid uptake capacity value of various samples may be simultaneously or sequentially assessed, as part of an automated scaled-up process appropriate for commercial production. In some embodiments, the apparatus and system provides for the specific selection of a desired sample possessing criteria as determined during such assessment, and optionally providing for transport of same to a desired location in said apparatus.

In some embodiments, according to this aspect, the process further comprises the step of contacting said marine organism skeletal derivative-based solid material with a fluid for from 0.5-15 minutes allowing for spontaneous fluid uptake of said fluid within said marine organism skeletal derivative-based solid material to arrive at said spontaneous fluid uptake value.

In some embodiments, according to this aspect, the process further comprises the step of contacting said marine organism skeletal derivative-based solid material with a fluid and applying negative pressure to said marine organism skeletal derivative-based solid material allowing for maximal uptake of said fluid within said marine organism skeletal derivative-based solid material to arrive at said total fluid uptake value.

In some embodiments, according to this aspect, the specific fluid uptake capacity value is a function of change in weight in said marine organism skeletal derivative-based solid material.

In some embodiments, according to this aspect, the specific fluid uptake capacity value is a function of change in fluid volume of applied fluid to said coralline-based solid material.

In some embodiments, the invention provides a solid substrate for facilitating cell or tissue growth or restored function in certain tissues, which solid substrate is characterized by a specific fluid uptake capacity value of less than 40%, which specific fluid uptake capacity value is determined by establishing a spontaneous fluid uptake value divided by a total fluid uptake value.

In some embodiments, this invention provides a solid substrate for promoting cell or tissue growth or restored function, which solid substrate comprises a marine organism skeletal derivative and is characterized by having a contact angle value of more than 60 degrees, when in contact with a fluid.

In some embodiments, the invention provides a solid substrate for mitigating cell or tissue adhesion or vascularization, or a process for obtaining same, which solid substrate comprises a organism skeletal derivative and is characterized by having a contact angle value of less than 60 degrees, when in contact with a fluid.

As the skilled artisan will appreciate, a contact angle may be determined as described and exemplified herein, using standard methodology and equipment, for example, via goniometry. In some embodiments, such methods may make use of processes as described in P. A. Thomson, W. B. Brinckerhoff, M. O. Robbins, in: K. L. Mittal (Ed.), Contact Angle Wettability and Adhesion, VSP, Utrecht, 1993, pp. 139-158; E. L. Decker, S. Garof, Langmuir 13 (1997) 6321; and M. G. Orkoula et al.: Colloids and Surfaces A: Physicochem. Eng. Aspects 157 (1999) 333-340; Hiemenz, P. C.; Rajagopalan, R. Principles of Colloid and Surface Chemistry, 1997, 3rd Ed., Marcel Dekker, Inc; Applied Colloid and Surface Chemistry Chapter 2: Surface Tension and wetting, by Richard Pashley, Marilyn Karaman, 2004, John Wiley and sons, all of which are hereby incorporated in their entirety.

In some embodiments, the invention provides a solid substrate for promoting cell or tissue growth or restored function, or a process for obtaining same, which solid substrate is characterized by substantial surface roughness (Ra) as measured by scanning electron microscopy or atomic force microscopy.

In some embodiments, the marine organism skeletal derivative-based solid material is substantially comprised of aragonite or calcite, or mixtures thereof or polymorphs of same. In some embodiments, the marine organism skeletal derivative is comprised substantially of aragonite, calcite, hydroxyapatite or a combination thereof.

In some embodiments the structure composition of the coral or coral derivative is determined by X-ray diffraction (XRD) or absence of appreciable Feigl solution staining.

In some embodiments, the solid substrate is isolated from a *Porites* species, a *Goniopora*, a *Millepora* species or an *Acropora* species.

In some embodiments, the solid substrate is isolated from a barnacle or mollusk. In some embodiments, the solid substrate is comprised of nacre.

In some embodiments, the invention provides a kit comprising one or more solid substrates as herein described. In some embodiments, the kit will comprise a series of solid substrates characterized by a specific fluid uptake capacity value of less than 45%, and/or produced by a process of this invention, where the marine organism skeletal derivative-based solid materials in the kit have a specific fluid uptake capacity value of and in some embodiments, the kit contains a series of solid substrates characterized by a specific fluid uptake capacity value of less than 40%, and in some embodiments, the kit contains a series of solid substrates characterized by a specific fluid uptake capacity value of less than 35%, and in some embodiments, the kit contains a series of solid substrates characterized by a specific fluid uptake capacity value of less than 30%, and in some embodiments, the the kit contains a series of solid substrates characterized by a specific fluid uptake capacity value of less than 20%. In some embodiments, the kit contains a series of solid substrates characterized by a specific fluid uptake capacity value of less than from 1-40%.

In some embodiments, this invention provides for the use of a marine organism skeletal derivative-based solid material as herein described, or a kit as herein described, for mitigating cell or tissue adhesion or vascularization, which in some embodiments represents a method or use of the invention. In some embodiments, such uses/methods may include use of a contact of an affected cell or tissue with a marine organism skeletal derivative-based solid material as herein described for decreasing angiogenesis in a subject, which in turn, in some embodiments, can serve as an effective therapy for such disorders as diabetic retinopathy, cancerous tumor growth, ocular neovascular disease, tumor formation and metastasis in tumors, hemangioma, ulcerative colitis, Crohn's disease, sickle cell anemia, sarcoid, syphilis, pseudoxanthoma elasticum, Paget's disease, vein occlusion, artery occlusion, carotid obstructive disease, chronic uveitis/ vitritis, mycobacterial infections, Lyme's disease, systemic lupus erythematosis, retinopathy of prematurity, Eale's disease, Bechet's disease, infections causing a retinitis or chorioiditis, presumed ocular histoplasmosis, Best's disease, myopia, optic pits, Stargardt's disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreoretinopathy and others as herein described. In some embodiments, the solid substrate is useful in preventing graft versus host disease or host versus graft disease. In some embodiments, the solid substrate is useful in promoting release of a therapeutic material over time located within said solid substrate and formulated for release from therewithin.

In some embodiments, this invention provides a process for selection of an optimized marine organism skeletal derivative-based solid substrate for mitigating cell or tissue adhesion or vascularization, said process comprising:

Isolating or preparing a marine organism skeletal derivative-based solid material;

contacting said marine organism skeletal derivative-based solid material with a fluid and establishing a contact angle for said marine organism skeletal derivative; and selecting a marine organism skeletal derivative-based solid material characterized by a contact angle of more than 60 degrees.

In some embodiments, according to this aspect, the process further comprises the step of contacting said marine organism skeletal derivative-based solid material with a fluid for from 0.1-15 minutes to promote spontaneous fluid uptake of said fluid within said marine organism skeletal derivative-based solid material to arrive at said spontaneous fluid uptake value. In some embodiments, the process comprises the step of contacting the marine organism skeletal derivative-based solid material with a fluid for from 12 up to 24 hours allowing for spontaneous fluid uptake of said fluid within said marine organism skeletal derivative-based solid material to arrive at said spontaneous fluid uptake value.

In some embodiments, according to this aspect, the process further comprises the step of contacting said marine organism skeletal derivative-based solid material with a fluid and applying negative pressure to said marine organism skeletal derivative-based solid material to promote maximal uptake of said fluid within said marine organism skeletal derivative-based solid material to arrive at said total fluid uptake value.

In some embodiments, according to this aspect, the specific fluid uptake capacity value is a function of change in weight in said marine organism skeletal derivative-based solid material.

In some embodiments, according to this aspect, the change in weight in said marine organism skeletal derivative-based solid material is due to absorbance of said fluid within interstices in said solid material, or in some embodiments, due to absorbance of said fluid within pores in said solid material, or in some embodiments, the change in weight in said marine organism skeletal derivative-based solid material is due to absorbance of said fluid within interstices in said solid material and due to absorbance of said fluid within pores in said solid material, which in some embodiments, is within or in some embodiments, between, individual coral crystals.

In some embodiments, according to this aspect, the specific fluid uptake capacity value is a function of change in fluid volume of applied fluid to said coralline-based solid material.

In some embodiments, the processes of this invention, which facilitate selection of an optimized organism skeletal derivative-based solid substrate for mitigating cell or tissue adhesion or vascularization may include a step whereby the contact of the organism skeletal derivative-based solid material with a fluid and establishing a contact angle for said organism skeletal derivative, or the establishing a specific fluid uptake capacity value of said marine organism skeletal derivative-based solid material, which specific fluid uptake capacity value is determined by establishing a spontaneous fluid uptake value divided by a total fluid uptake value may be performed on samples immediately proximal to a sample of interest, and in some embodiments, from within a comparable region, for example, in terms of a region of coral growth in a growth ring, with the selection envisioned to be based in some embodiments, on the performance of proximal regions, and their achievement of the desired criteria for selection, as herein described.

In some embodiments, the marine organism skeletal derivative-based solid material is substantially comprised of calcium carbonate.

In some embodiments the invention provides a process for isolating/preparing an optimized marine organism skeletal derivative-based solid substrate for mitigating cell or tissue adhesion or vascularization comprising the steps of:

establishing the presence of a substantially smooth surface on a marine organism skeletal derivative-based solid material, which substantially smooth surface is determined by scanning electron microscopy or atomic force microscopy; and selecting a marine organism skeletal derivative-based solid material characterized by a determination of the presence of a substantially smooth surface on said marine organism skeletal derivative-based solid material.

In some embodiments, the invention provides for a combination of steps as described for the processes contemplated herein.

In other embodiments, the invention provides for a process for isolating/preparing an optimized marine organism skeletal derivative-based solid substrate for mitigating cell or tissue adhesion or vascularization comprising the steps of establishing the lack of positive staining by Feigl stain, for example, in accordance with the methods as described in: Chemical staining methods used in the identification of carbonate minerals, Tamer AYAN, Mineral Research and Exploration Institute of Turkey www.mta.gov.tr/v2.0/eng/dergi_pdf/65/11.pdf, which reference is hereby incorporated in its entirety.

In some embodiments, in accordance with any described process of this invention, such process further comprises the step of placing said solid substrate in proximity with cells or tissue, at a desired site of insertion, whereby mitigation or prevention of cell or tissue adhesion occurs at said site, or mitigation or prevention of vascularization at said site occurs.

In some embodiments, according to this aspect, the fluid is a protein-containing, salt-containing or carbohydrate containing solution, or in some embodiments, the fluid is a biologic fluid, and in some embodiments, the biologic fluid is autologous or allogeneic with respect to a cell or tissue of a subject when said solid substrate is contacted with a cell or tissue of said subject. In some embodiments, the fluid is water.

In some embodiments, the solid substrate prevents cell or tissue growth within or proximal to the insertion/placement of said solid substrate.

In some embodiments, the invention provides a solid substrate produced by the process according to any aspect as herein described.

In some embodiments, the marine organism skeletal derivative-based solid material approximates the form of a cylinder, cone, tac, pin, screw, rectangular bar, plate, disc, pyramid, granule, powder, coral sand, ball, bone, condyle, rib, vertebra, valve, prosthesis, coating for a prosthesis, stent or cube. In some embodiments, the marine organism skeletal derivative-based solid material approximates a shape which accommodates a site of desired tissue growth or repair. In some embodiments, the marine organism skeletal derivative-based solid material comprises a hollow or hollows along a Cartesian coordinate axis of said coralline-based solid material.

In some embodiments, the invention provides a solid substrate produced by the process according to any aspect as herein described.

All publications, patents, and patent applications mentioned herein are hereby incorporated by reference in their entirety as if each individual publication or patent was specifically and individually indicated to be incorporated by reference. In case of a conflict between the specification and an incorporated reference, the specification shall control. Where number ranges are given in this document, endpoints are included within the range. Furthermore, it is to be understood that unless otherwise indicated or otherwise evident from the context and understanding of one of ordinary skill in the art, values that are expressed as ranges can assume any specific value or sub-range within the stated ranges, optionally including or excluding either or both endpoints, in different embodiments of the invention, to the tenth of the unit of the lower limit of the range, unless the context clearly dictates otherwise. Where a percentage is recited in reference to a value that intrinsically has units that are whole numbers, any resulting fraction may be rounded to the nearest whole number.

BRIEF DESCRIPTION OF THE DRAWINGS

FIG. 1 provides a series of photographs of implants, which were assessed for their ability to imbibe a biologic fluid, in this case, whole human blood.

FIG. 2 presents a flow chart for an embodied screening protocol for the identification of optimized marine organism skeletal derivative-based solid substrates for mitigating or preventing cell or tissue adhesion and vascularization.

FIG. 3 C indicates a similar specimen to FIG. 2 A with high fluid uptake capacity. The surface is covered by crystals.

FIG. 8 demonstrates the microscopic structure as determined by ESEM, of isolated substrates characterized by minimal biologic fluid uptake, versus those characterized by substantial biologic fluid uptake at various magnifications in samples with minimal biologic fluid uptake indicate a much smoother external surface as compared to samples with substantial uptake (FIGS. 8A-8C versus 8D-8F).

FIGS. 11A and 11B schematically depict an embodied automated apparatus of this invention in side and top view.

DETAILED DESCRIPTION OF THE PRESENT INVENTION

Figure 1A:
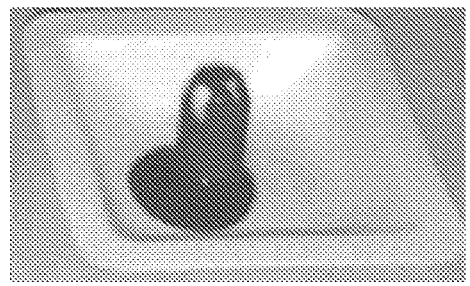
FIGS. 1A-1C show 3 types of patterns of uptake within small coral solid substrate samples, reasonably full uptake as determined by surface color change observation, moderate uptake and minimal uptake, respectively.

This invention provides, inter alia, processes for selecting for and obtaining optimized solid substrates for optimized solid substrates for mitigating or preventing cell or tissue growth or mitigating or preventing vascularization and materials obtained thereby.

In some embodiments, the invention provides a solid substrate for mitigating or preventing cell or tissue adhesion or vascularization, which solid substrate comprises marine organism skeletal derivative and is characterized by a specific fluid uptake capacity value of less than 40%, which specific fluid uptake capacity value is determined by establishing a spontaneous fluid uptake value divided by a total fluid uptake value.

In some embodiments, the invention provides a solid substrate for mitigating cell or tissue adhesion and vascularization, which solid substrate comprises marine organism skeletal derivative and is characterized by having a contact angle value of more than 60 degrees, when in contact with a fluid.

In some embodiments, the invention provides a solid substrate for promoting cell or tissue growth or restored function, which solid substrate comprises a marine organism skeletal derivative and is characterized by minimal surface roughness (Ra), or a smooth surface, as measured by scanning electron microscopy or atomic force microscopy.

The solid substrates of this invention will comprise a marine organism skeletal derivative-based material.

In some embodiments, the term "marine organism skeletal derivative-based material" refers to a solid piece or ground material derived from a marine organism, and from a skeletal component of the organism, such as an exoskeleton of the same, which in some embodiments, is further processed to be suitable for implantation in a human or veterinary subject, and further processed to be optimized for implantation as described herein.

In some embodiments, the term "marine organism skeletal derivative-based material" refers to a coralline-based material further processed to be suitable for implantation in a human or veterinary subject, and further processed to be optimized for implantation as described herein.

Coral, which is mainly comprised of $CaCO_3$ has been shown to possess the advantage of supporting fast cellular invasion, adherence and proliferation. As demonstrated herein, certain coral samples, however have been shown to be an effective substrate for mitigating or abrogating adherence, proliferation and differentiation of certain cells and tissue.

The terms "coral" and "calcium carbonate" and "aragonite" and "calcite" may be used interchangeably herein.

In some embodiments, the term "marine organism skeletal derivative-based material" refers to a coral or coral derivative further processed to be suitable for implantation in a human or veterinary subject, and further processed to be optimized for implantation and for the therapeutic applications as described hereinunder.

In some embodiments, the term "marine organism skeletal derivative-based material" refers to barnacle or mollusk-derived skeletal material further processed to be suitable for implantation in a human or veterinary subject, and further processed to be optimized for implantation as described hereinunder, and in some embodiments, inclusion of nacre further processed to be suitable for implantation in a human or veterinary subject, and further processed to be optimized for implantation as described hereinunder is contemplated.

In some embodiments, the term "marine organism skeletal derivative-based material" refers to a coralline-based material. As exemplified herein, certain coral isolates, have been shown to resist specific fluid uptake of biologic fluids. While regions of coral with high specific fluid uptake of biologic fluids have been shown to be effective substrates for facilitation of the adherence, proliferation and differentiation of mesenchymal stem cells, and ultimate incorporation into cartilage and/or bone tissue, as denoted herein there is a heterogeneity in coral samples, whereby certain sections of coral which are relatively impervious to specific fluid uptake of biologic fluids, similarly appear to mitigate cell or tissue adhesion to such substrate, which ultimately negatively impacts vascularization, as well. Such samples may be further processed, as described herein to alternatively improve their absorption profile, or in preferred embodiments herein, to specifically further mitigate or entirely abrogate cell adhesion to such substrate.

In some embodiments, the solid substrate contains ground particles derived from coral, suspended in a biocompatible matrix. In some embodiments, the biocompatible matrix is a hydrogel. In some embodiments the marine organism skeletal derivative-based material comprises a bone graft or bone substitute material.

In some embodiments, reference to an "implant" or "plug" or "solid substrate", as used herein refers to any embodiment or combined embodiments as herein described with regard to the solid substrates and to be considered as being included in the described aspect of this invention. For example, reference to a "solid substrate" as used herein, is to be understood to refer to any embodiment of a solid substrate as described herein being applicable for the indicated purpose or containing the indicated attribute, etc.

In one embodiment, "solid substrate" refers to a shaped platform used for cell and/or tissue repair and/or restored function, wherein the shaped platform provides a site for such repair and/or restored function. In one embodiment, the solid substrate is a temporary platform. In one embodiment, "temporary platform" refers to a natural degradation of a coral of this invention that occurs over time during such repair, wherein the natural fully or partially degradation of the coral may results in a change of solid substrate shape over time and/or change in solid substrate size over time.

It will be appreciated that different species of coral vary in terms of their average pore diameter and pore volume and the invention contemplates use of any such coral as a starting material for the preparation of the solid substrates as herein described, where the solid substrate is characterized in that it is characterized by a specific fluid uptake capacity value of less than 40%, or is characterized by having a contact angle value of more than 60 degrees, when in contact with a fluid.

As used herein, the term "pore volume" refers to volume or open spaces inside the porous scaffolding of this invention. Pore volume is determined by any means known in the art. Porosity can be calculated by standard methods, an example of which is provided further hereinbelow, see for example, Karageorgiou V, Kaplan D. (2005) "Porosity of 3D biomaterial scaffolds and osteogenesis" Biomaterials.; 26(27):5474-91, which is hereby incorporated by reference in its entirety.

It will be appreciated that the term "coral" will refer to a starting material from which aragonite, calcium carbonate, calcite, etc. may be isolated.

The terms "coral" and "aragonite" and "calcite" may be used interchangeably herein.

In some embodiments, the term "marine organism skeletal derivative-based material" refers to a coral or coral derivative. In some embodiments, the term "marine organism skeletal derivative-based material" refers to barnacle or mollusk-derived skeletal material, and in some embodiments, inclusion of nacre is contemplated. In some embodiments, sponge or soft coral is contemplated for use. In some embodiments, the marine organism skeletal derivative-based material refers to inclusion of bone, decalcified bone, ivory or dentin, as well.

In some embodiments, the solid substrate contains ground particles derived from coral, suspended in a biocompatible matrix. In some embodiments, the biocompatible matrix is a hydrogel.

It will be appreciated that the term "coral" will refer to a starting material from which aragonite, calcium carbonate, calcite, or hydroxyapatite etc. may be isolated and further processed to be suitable for implantation in a human or veterinary subject, and further processed to be optimized for implantation as described hereinunder.

In one embodiment, the solid substrates, processes and/or kits of this invention employ use of a coral further processed to be suitable for implantation in a human or veterinary subject, and further processed to be optimized for implantation as described hereinunder. In one embodiment, the coral comprise any species, including, inter alia, *Porites, Acropora, Goniopora, Millepora*, or a combination thereof. In another embodiment the solid substrates, processes and/or kits of this invention employ use of nacre, molusc shell, or bone morsels.

In one embodiment, the solid substrates, processes and/or kits of this invention employ use of a coral. In one embodiment, the coral comprise any species, including, inter alia, *Porites, Acropora, Goniopora, Millepora*, or a combination thereof. In another embodiment the solid substrates, processes and/or kits of this invention employ use of nacre, molusc shell, or bone morsels.

In one embodiment, the coral is from the *Porites* species. In one embodiment, the coral is *Porites lutea*. In one embodiment, the coral is from the *Acropora* species. In one embodiment, the coral is *Acropora grandis*, which in one embodiment is very common, fast growing, and easy to grow in culture. Thus, in one embodiment *Acropora* samples can be easily collected in sheltered areas of the coral reefs and collection from the coral reefs can be avoided by use of cultured coral material.

In another embodiment, the coral is from the *Millepora* species. In one embodiment, the coral is *Millepora dichotoma*. In one embodiment, the coral has a pore size of 150 µm and can be cloned and cultured, making Millerpora useful as a framework in the solid substrates, methods and/or kits of this invention.

In one embodiment, the coral is from the *Goniopora* species. In some embodiments, the coral is *Goniopora albiconus, Goniopora burgosi, Goniopora cellulosa, Goniopora ceylon, Goniopora ciliatus, Goniopora columna, Goniopora djiboutiensis, Goniopora eclipsensis, Goniopora fruticosa, Goniopora gracilis, Goniopora klunzingeri, Goniopora lobata, Goniopora mauritiensis, Goniopora minor, Goniopora norfolkensis, Goniopora palmensis, Goniopora pandoraensis, Goniopora parvistella, Goniopora pearsoni, Goniopora pendulus, Goniopora planulata, Goniopora polyformis, Goniopora reptans, Goniopora savignyi, Goniopora somaliensis, Goniopora stokes, Goniopora stutchburyi, Goniopora sultani, Goniopora tenella, Goniopora tenuidens* or *Goniopora viridis*.

In another embodiment, the coral is from any one or more of the following species *Favites halicora; Goniastrea retiformis; Acanthastrea echinata; Acanthastrea hemprichi; Acanthastrea ishigakiensis; Acropora aspera; Acropora austera; Acropora* sp. "brown digitate"; *Acropora carduus; Acropora cerealis; Acropora chesterfieldensis; Acropora clathrata; Acropora cophodactyla; Acropora* sp. "danai-like"; *Acropora divaricata; Acropora donei; Acropora echinata; Acropora efflorescens; Acropora gemmifera; Acropora globiceps; Acropora granulosa; Acropora* cf *hemprichi; Acropora kosurini; Acropora* cf *loisettae; Acropora longicyathus; Acropora loripes; Acropora* cf *lutkeni; Acropora paniculata; Acropora proximalis; Acropora rudis; Acropora selago; Acropora solitaryensis; Acropora* cf *spicifera* as per *Veron; Acropora* cf *spicifera* as per *Wallace; Acropora tenuis; Acropora valenciennesi; Acropora vaughani; Acropora vermiculata; Astreopora gracilis; Astreopora myriophthalma; Astreopora randalli; Astreopora suggesta; Australomussa rowleyensis; Coscinaraea collumna; Coscinaraea crassa; Cynarina lacrymalis; Distichopora violacea; Echinophyllia echinata; Echinophyllia* cf *echinoporoides; Echinopora gemmacea; Echinopora hirsutissima; Euphyllia ancora; Euphyllia divisa; Euphyllia yaeyamensis; Favia rotundata; Favia truncatus; Favites acuticollis; Favities pentagona; Fungia granulosa; Fungia klunzingeri; Fungia mollucensis; Galaxea acrhelia; Goniastrea edwardsi; Goniastea minuta; Hydnophora pilosa; Leptoseris explanata; Leptoseris incrustans; Leptoseris mycetoseroides; Leptoseris scabra; Leptoseris yabei; Lithophyllon undulatum; Lobophyllia hemprichii; Merulina scabricula; Millepora dichotoma; Millepora exaesa; Millipora intricata; Millepora murrayensis; Millipora platyphylla; Monastrea curta; Monastrea colemani; Montipora caliculata; Montipora capitata; Montipora foveolata; Montipora meandrina; Montipora tuberculosa; Montipora* cf *vietnamensis; Oulophyllia laevis; Oxypora crassispinosa; Oxypora lacera; Pavona bipartita; Pavona venosa; Pectinia alcicornis; Pectinia paeonea; Platygyra acuta; Platygyra pini; Platygyra* sp "green"; *Platygyra verweyi; Podabacia* cf *lanakensis; Porites annae; Porites cylindrica; Porites evermanni; Porites monticulosa; Psammocora digitata; Psammocora explanulata; Psammocora haimeana; Psammocora superficialis; Sandalolitha dentata; Seriatopora caliendrum; Stylocoeniella armata; Stylocoeniella guentheri; Stylaster* sp.; *Tubipora musica; Turbinaria stellulata;* or any coral known in the art, or a combination thereof.

In another embodiment, derivatives of marine animals such as coral, sponges, moluscs shells, bone matrix, ivory, dentin and other related organisms and tissues may be used in the solid substrates, methods and/or kits of this invention may be *Madreporaria, Helioporida* of the order *Coenothecalia, Tubipora* of the order *Stolonifera, Millepora* of the order *Milleporina*, or others known in the art. In some embodiments, coral for use in the substrates, methods and/or kits of this invention may comprise scleractinian coral, including in some embodiments, *Goniopora* and others. In some embodiments, coral for use in the substrates, methods and/or kits of this invention may comprise *Alveoppora*. In some embodiments, coral for use in the substrates, methods and/or kits of this invention may comprise bamboo corals, including in some embodiments, coral from the family Isididae, genera *Keratoisis, Isidella*, and others.

In one embodiment of this invention, the term "coral" refers to coral which is cut from a single piece of coral and further processed to be suitable for implantation in a human or veterinary subject, and still further processed to be optimized for implantation as described herein.

In some embodiments, the solid substrate is of any desired shape.

In one embodiment, coral may be machined into a variety of configurations, and quite complex shapes such as cylindrical structures and threaded structures may be formed by appropriate machine or other processing, such as chemical processing. In another embodiment, coral may be shaped to form solid blocks, rods or granular forms. In one embodiment, corallin materials are shaped in such a way as to conform to the shape of a desired tissue structure or to optimally prevent contact with a material embedded or contained therewithin, when implanted within a potential implantation site. In one embodiment, coral is implanted in an orientation that allows it to contact the maximum surface area of an adjacent-located desired structure.

In some embodiments, the solid substrate approximates the form of a cylinder, cone, tac, pin, screw, rectangular bar, plate, disc, pyramid, granule, powder, coral sand, ball, bone, condyle, rib, vertebra, valve, prosthesis, coating for a prosthesis, stent or cube. In some embodiments, the solid substrate approximates a shape which accommodates a site of desired tissue growth or repair.

In some embodiments, the solid substrate comprises a hollow or hollows along a Cartesian coordinate axis of said solid substrate.

In one embodiment, the size of coral solid substrates may be any size that would be useful for the purposes of the present invention, as would be known to one of skill in the Art depending on the purpose. For example and in one embodiment, the solid substrate may be substantially the same size as the structure it is meant to replace, while in another embodiment, the solid substrate or a portion thereof may be the size sufficient to encase a tissue or matter, such that it may be placed within a region in a subject to regulate access to the material encased therein in a discrete location.

In one embodiment, coral is washed, bleached, frozen, dried, exposed to electrical forces, magnetic forces or ultrasound waves or microwaves or electromagnetic radiation or high pressure or a combination thereof prior to use thereof. According to this aspect, and in some embodiments, the coral is exposed to further processing, as described hereinunder.

In some embodiments, the solid substrate is of a size that is appropriate for the intended purpose, as will be appreciated by the skilled artisan.

In some embodiments, the solid substrate is of a size that is appropriate for the intended purpose, as will be appreciated by the skilled artisan. For example, and in some embodiments, solid substrates for use in osteochondral therapy or repair may make use of a substrate that is cylindrical or oval in shape and has a diameter of about 5-15 mm, and a height of about 5-25 mm. In some embodiments, the solid substrate has a diameter of about 1-35 mm, and a height of about 1-45 mm, or about 5-40 mm, and a height of about 5-60 mm, or about 5-15 mm, and a height of about 5-45 mm 5-30 mm, 15-60 mm, or larger. It will be appreciated by the skilled artisan that the size of the substrate may be so selected so as to be suitable to a particular application, for example, when using as a scaffolding material for bone repair, then the size may approximate the dimensions of a long bone in the subject. Accordingly, this invention is not to be limited by the size of the solid substrate.

For example, and in some embodiments, solid substrates of this invention and/or for use in the kits and methods as described may make use of a substrate that is cylindrical or oval in shape and in some embodiments, solid substrates of this invention and/or for use in the kits and methods as described may have a diameter in the nanometer or micrometer scale. In some embodiments, solid substrates for use in the anti-cancer or other described applications may make use of a substrate that is cylindrical or oval in shape and has a diameter of about 1-100 nm, or in some embodiments, having a diameter of about 50-1000 nm, or in some embodiments, having a diameter of about 10-2000 nm, or in some embodiments, having a diameter of about 100-4000 nm. In some embodiments, solid substrates for use in for use in the anti-cancer or other described applications may make use of a substrate that is cylindrical or oval in shape and has a diameter of about 1-100 µm, or in some embodiments, having a diameter of about 50-1000 µm, or in some embodiments, having a diameter of about 10-2000 µm, or in some embodiments, having a diameter of about 100-4000 µm.

For example, and in some embodiments, solid substrates of this invention and/or for use in the kits and methods as described may make use of a substrate that is cylindrical or oval in shape and in some embodiments, solid substrates of this invention and/or for use in the kits and methods as described may have a diameter in the millimeter or centimeter scale. In some embodiments, solid substrates for use for use in the anti-cancer or other described applications may make use of a substrate that is cylindrical or oval in shape and has a diameter of about 1-100 mm, or in some embodiments, having a diameter of about 50-1000 mm, or in some embodiments, having a diameter of about 10-2000 mm, or in some embodiments, having a diameter of about 100-4000 mm. In some embodiments, solid substrates for use in for use in the anti-cancer or other described applications may make use of a substrate that is cylindrical or oval in shape and has a diameter of about 1-100 cm, or in some embodiments, having a diameter of about 50-1000 cm, or in some embodiments, having a diameter of about 10-2000 cm, or in some embodiments, having a diameter of about 100-4000 cm.

It will be appreciated by the skilled artisan that the size of the substrate may be so selected so as to be suitable to a particular application. Accordingly, this invention is not to be limited by the size of the solid substrate. The average diameter of the voids within the phases of the solid substrates of this invention may be determined by any means, including digital images analysis.

In some embodiments, the coral for use in accordance with the instant invention may be prepared as described in PCT International Application publication Number WO 2009/066283, PCT International Application publication Number WO 2010/058400, PCT International Application publication Number WO 2010/146574 and PCT International Application publication Number WO 2010/146574, each of which is fully incorporated by reference herein, in its entirety.

In other embodiments the marine organism skeletal derivative, such as coral, may be ground up and used to prepare the solid substrates of this invention.

In some embodiments, coral is isolated from a natural source by known methods, and as described herein. In some embodiments, care is taken to isolate coral slices from a region of one or more growth rings within a larger coral sample, which region has been shown to possess the appropriate specific fluid uptake capacity value, the appropriate contact angle value and/or surface roughness, as described herein and in some embodiments, is then exposed to further processing as described hereinunder.

In other embodiments the marine organism skeletal derivative, such as coral may be decalcified and the organic matrix isolated, for example by dialysis. Such processed substrates may then be used alone or with the addition of calcium carbonate.

In other embodiments the coral may be converted fully or partially into hydroxyapatite, and then evaluated for the indicated specific uptake value or contact angle, and in some embodiments, the coral is first evaluated for the indicated specific uptake value or contact angle of the same and then converted into hydroxyapatite. In some embodiments coral dialysate or ground coral may be prepared as a layer which serves as a surface covering for hydroxyapatite.

In some embodiments, a solid substrate of this invention is characterized by a specific fluid uptake capacity value as desired for the specific application for example of less than 40%, which specific fluid uptake capacity value is determined by establishing a spontaneous fluid uptake value divided by a total fluid uptake value.

As described and exemplified herein, for example, as described in Example 1 and 3, a specific fluid uptake capacity value may be determined by evaluating spontaneous uptake of a fluid versus a total uptake capacity for a given sample and arriving at the specific fluid uptake capacity level, whereby if the value is less than 40%, then such solid substrate will be used in applications mitigating or preventing cell and tissue growth and/or vascularization.

In some embodiments, the process for selection of the solid substrate comprises isolating a sample of a coralline-based solid material and establishing a specific fluid uptake capacity value of the material, which specific fluid uptake capacity value is determined by establishing a spontaneous fluid uptake value divided by a total fluid uptake value and selecting material characterized by a specific fluid uptake capacity value of less than 40%.

In some embodiments, the biologic fluid is blood, and in some embodiments, the biologic fluid is water. In some embodiments, the biologic fluid is a protein-containing, salt-containing or carbohydrate containing solution.

In some embodiments, according to this aspect, such solid substrates may have a preferentially higher affinity for hydrophobic fluids.

In some embodiments, the biologic fluid is autologous with respect to a cell or tissue of a subject when said solid substrate is contacted with such cell or tissue of said subject.

It will be understood that the biologic fluid may be any fluid which is biocompatible and whose incorporation is appropriate within a solid substrate for the desired application.

In some embodiments, the process further comprises the step of contacting the material with a fluid for from 2-15 minutes to promote spontaneous fluid uptake of said fluid within said coralline-based solid material to arrive at said spontaneous fluid uptake value. In some embodiments, the process may allow for the contacting of the material with a fluid for from 0.5-15 minutes, or in some embodiments, from 0.5-5 minutes, or in some embodiments, 10-60 minutes, or in some embodiments, from 60 to 90 minutes, or in some embodiments, other intervals, to promote spontaneous fluid uptake. The skilled artisan will appreciate that the amount of time for which the fluid is applied to determine the spontaneous uptake may be extended or shortened as a function of the dimensions and geometry of the sample substrate being assessed. In some embodiments, when a larger sample is being assessed, the process further comprises the step of contacting the material with a fluid for from 2-24 hours to promote spontaneous fluid uptake of said fluid within said coralline-based solid material to arrive at said spontaneous fluid uptake value.

In some embodiments, the process further comprises the step of contacting said marine organism skeletal derivative-based solid material with a fluid and applying negative pressure to said coralline-based solid material to promote maximal uptake of said fluid within said coralline-based solid material to arrive at said total fluid uptake value. In some embodiments, application of negative pressure is via the application of a vacuum to the substrate immersed in the fluid, promoting entry of the fluid therewithin.

In some embodiments, the process may further comprise the step of contacting said coralline-based solid material with a fluid and applying positive pressure to said coralline-based solid material to promote maximal uptake of said fluid within said coralline-based solid material to arrive at said total fluid uptake value. According to this aspect, and in some embodiments, care will be taken to ensure that the application of pressure does not in any way compromise the structural integrity of the solid substrate. In other embodiments, pressure application may further serve to render the solid substrate into a ground particulate state.

In some embodiments, application of positive pressure is via any manual means, for example, via the use of any applicator, syringe, etc., gravitational pressure, and others, as will be appreciated by the skilled artisan. In some embodiments, application of positive pressure is via forced osmosis, centrifugation and others. In some embodiments, combinations of the described methods and others are envisioned.

In some embodiments, a prescreening step may be undertaken. For example, and in some embodiments, a coral slice of a desired thickness is taken, which for example may be perpendicular to the coral sample ring growth. The slice may be evaluated for rapid uptake of a biological fluid, such as, for example, uptake of a colored proteinaceous fluid, such as blood. In some embodiments, blood from any source may be used, such as, for example, from livestock or other sources. According to this aspect, and in some embodiments, samples are selected, which samples do not show appreciative uptake of the indicated fluid, or in some embodiments, do not appreciably stain positive with Feigl solution, as herein described.

Samples which provide reduced or minimal uptake as part of the described prescreen procedure may be further assessed for their specific fluid uptake capacity value.

For example, and in some embodiments, smaller samples or specific scaffolds may be isolated from the block from which the coral slice was taken for prescreening, from regions which were determined by the prescreen to provide diminished or no appreciable uptake of the biological fluid.

In some embodiments, scaffold and/or smaller samples are dried and then subjected to further processing. Such further processing, for example, ensures removal of matter, which would render the implants unfit for implantation in human or veterinary subjects. In some embodiments, such processing produces a product that is fit for implantation, in accordance with regulatory body guidances, such as, for example, the ASTM F 1185-03: Standard Specification for Composition of Hydroxylapatite for Surgical Implants, or ASTM F 1581-08: Standard Specification for Composition of Anorganic Bone for Surgical Implants.

In some embodiments, such further processing includes the reduction of organic residuals in the scaffold and/or smaller samples, and subsequent elimination of the agent used. In some aspects, such agents may include sodium hypochlorite, hydrogen peroxide (solutions thereof) or use of both, which in some embodiments, is followed by the application of a non-polar solvent.

In some embodiments, such further processing steps may be undertaken following the establishment of a specific fluid uptake capacity value and in some embodiments, such further processing steps may be undertaken prior to establishing the specific fluid uptake capacity value for the sample(s).

According to this aspect, and in some embodiments, such scaffold or smaller samples may be fully dried, and then assessed for their spontaneous fluid uptake value, for example, as described in Example 1 below. For example, the dry sample may be immersed in water and the spontaneous fluid uptake value assessed, followed by an assessment of the total fluid uptake value. According to this aspect, and in one embodiment, samples producing a specific fluid uptake capacity value of less than 40% are selected for further processing. In some embodiments, samples producing a specific fluid uptake capacity value of from 1-35% are selected for still further processing.

In some embodiments, this solid substrate for promoting cell or tissue growth or restored function comprises a marine organism skeletal derivative characterized by having a contact angle value of more than 60 degrees, when in contact with a fluid.

Example 2 demonstrated that solid substrates characterized by a contact angle value of more than 60 degrees is comparable to samples having a specific fluid uptake capacity value of less than 40%, and therefore such samples are also to be considered as comprising part of this invention.

Methods for determining a contact angle are well known, and any appropriate method can be used. One embodiment of such a method is provided herein with regard to Example 3.

Similarly, in some embodiments of this invention, there is provided a process for selection of an optimized marine organism skeletal derivative-based solid substrate for an optimized marine organism skeletal derivative-based solid substrate for mitigating cell or tissue adhesion and vascularization, said process comprising:
  isolating or preparing a marine organism skeletal derivative-based solid material;
  contacting said marine organism skeletal derivative-based solid material with a fluid and establishing a contact angle for said marine organism skeletal derivative; and
  selecting a marine organism skeletal derivative-based solid material characterized by a contact angle of more than 60 degrees.

In some embodiments, coral-based solid substrates of this invention may be converted to hydroxyapatite by known methods.

According to this aspect, a solid substrate characterized by a specific fluid uptake capacity value of less than 40%, which specific fluid uptake capacity value is determined by establishing a spontaneous fluid uptake value divided by a total fluid uptake value may be converted to hydroxyapatite, and the indicated activity is present in the converted substrate.

In another embodiment, solid substrate characterized by having a contact angle value of greater than 60 degrees, when in contact with a fluid may be converted to hydroxyapatite, and the indicated activity is present in the converted substrate.

In another aspect, a solid substrate is converted to hydroxyapatite, and the same is then assessed for the presence of a specific fluid uptake capacity value of less than 40%, which specific fluid uptake capacity value is determined by establishing a spontaneous fluid uptake value divided by a total fluid uptake value, and such substrates fulfilling the stated criteria are specifically selected and encompassed by the subject application.

In another aspect, a solid substrate is converted to hydroxyapatite, and the same is then assessed in terms of its contact angle and whether the angle is more than 60 degrees, and such substrates fulfilling the stated criteria are specifically selected and encompassed by the subject application.

In some embodiments, the specific fluid uptake capacity value is a function of change in weight in said coralline-based solid material.

In some embodiments, solid substrates as herein defined, such as, for example, coral samples or nacre or others as herein described are assessed by selecting a small dry sample for use in the processes as herein described, whose region of isolation from a larger block may be ascertained, in order to provide information regarding the characteristics of the area in the block from which additional samples may be isolated and then used.

In some aspects, the sample is dried under vacuum and/or heated.

In some embodiments, when assessing the specific fluid uptake capacity value, the dry weight for each sample is recorded and fluid as described herein is added an assay container.

In some embodiments, when assessing the specific fluid uptake capacity value, at least 1:1 ratio of the size of the sample in mm to the volume of fluid added in ml is applied to the container. In some embodiments, the amount of fluid applied is in excess, as compared to the sample size.

In some embodiments, when assessing the specific fluid uptake capacity value, once the initial fluid uptake is assessed, according to this aspect and in some embodiments, the solid substrate sample is then brought into contact with the fluid and the weight of the solid substrate sample is assessed.

In some embodiments, when assessing the specific fluid uptake capacity value, spontaneous fluid uptake is assessed and a spontaneous fluid uptake value is established, based on the change in weight of the sample.

In some embodiments, when assessing the specific fluid uptake capacity value, the specific fluid uptake capacity value is a function of change in fluid volume of applied fluid to said marine organism skeletal derivative-based solid material. According to this aspect, spontaneous fluid uptake is assessed and a spontaneous fluid uptake value is established based on the uptake of the volume applied to the sample.

In some embodiments, when assessing the specific fluid uptake capacity value, the process further comprises contacting the sample with a significantly increased amount of fluid and applying pressure thereto to promote maximal fluid uptake to the total fluid uptake capacity of the sample.

In some embodiments, when assessing the specific fluid uptake capacity value, as noted, such pressure may be either positive or negative pressure, and the application time is for a period of time sufficient to ensure maximal uptake of the applied fluid into the marine organism skeletal derivative sample.

In some embodiments, such time may include an interval of from 0.5-60 minutes, or in some embodiments, when a larger sample is being assessed, such time may include an interval of from 2-24 hours to arrive at said spontaneous fluid uptake value. It will be appreciated that the time intervals recited herein are applicable for any embodiment with regard thereto as described herein. The skilled artisan will appreciate that the amount of time for which the fluid is applied to determine the full capacity fluid uptake may be extended or shortened as a function of the dimensions and geometry of the sample substrate being assessed.

According to these aspects, the total fluid uptake capacity is thus assessed and the specific fluid uptake capacity value is then determined.

In some embodiments, the invention specifically contemplates solid substrates having a specific fluid uptake capacity value characterized by having a value less than the cutoff value of 40%, for the sample to be noted optimized as a solid substrate for mitigating or preventing cell or tissue growth and/or vascularization. It will be appreciated that the invention contemplates the stated cutoff value for promoting a reasonable value that reduces the presence of appreciable false positives, i.e. solid substrates that are not as optimal for the stated applications.

In some embodiments, the invention specifically contemplates solid substrates characterized by having a contact angle value of more than 60 degrees, when in contact with a fluid, for the sample to be noted optimized as a solid substrate for mitigating cell or tissue adhesion and vascularization. It will be appreciated that the invention contemplates the stated cutoff value for promoting a reasonable value that reduces the presence of appreciable false positives, i.e. solid substrates that are not as optimal for the stated applications.

It is to be noted that the usefulness for select coralline substrates characterized by a different specific fluid uptake capacity value for promoting tissue growth such as cartilage and bone has been previously shown. Surprisingly, it has now been found that while numerous coral-based substrates isolated can be used for such repair, isolates of marine organism skeletal derivatives, for example, characterized by a specific fluid uptake capacity value of less than 40% provide a different phenomenon, and actually mitigate cell or tissue adhesion or vascularization in cells and tissue located proximally thereto.

Without being bound by theory, and representing non-limiting embodiments of the substrates, processes and applications of this invention, specific selection of marine organism skeletal derivative-based solid substrates characterized by the desired specific fluid uptake capacity value of less than 40%, or specific selection of marine organism skeletal derivative-based solid substrates characterized by having a contact angle value of more than 60 degrees, when in contact with a fluid, may select for a sample whose vascularization is diminished, or in some embodiments, whose access to lymph is diminished, or in some embodiments, whose specific structural and/or chemical makeup specifically creates a privileged site such that extravasation of blood cells and other cells thereunto is mitigated. It is to be understood that any of these mechanisms, and others, may account for the phenomenon of diminished cell or tissue adhesion or vascularization, and that any such mechanism associated with the application of an optimized marine organism skeletal derivative-based solid substrate for promoting cell or tissue growth or restored function characterized by a specific fluid uptake capacity value of less than 40% is to be understood as being part of this invention.

In some embodiments, samples thus processed and found to be characterized by a specific fluid uptake capacity value of less than 40%, or specific selection of marine organism skeletal derivative-based solid substrates characterized by having a contact angle value of more than 60 degrees, when in contact with a fluid, may then be used for the isolation of proximally located regions of a section from which such sample was taken, which samples can then be reliably used and considered as being optimized in accordance with the processes of this invention. In some embodiments, with regard to coral-based samples, such regions may include the entire annual growth ring region within the coral from which the sample was derived.

In some embodiments, samples thus processed and found to be characterized by a specific fluid uptake capacity value of less than 40%, or specific selection of marine organism skeletal derivative-based solid substrates characterized by having a contact angle value of more than 60 degrees, when in contact with a fluid, may then be dried fully and utilized for implantation into a subject for mitigating cell or tissue adhesion and vascularization at a site of treatment/implantation.

In some embodiments, the samples thus processed and found to be characterized by a specific fluid uptake capacity value of less than 40%, or specific selection of marine organism skeletal derivative-based solid substrates characterized by having a contact angle value of more than 60 degrees, when in contact with a fluid, or having a desired surface smoothness may select for a sample which is particularly useful in promoting ex-vivo three-dimensional support and structure for certain cell, tissue or organ growth. In some embodiments, such cell, tissue or organ growth may include that for connector tissues, such as tendon and ligament, heart, muscle, liver, kidney, skin, blood vessel and neuronal growth and development.

In some embodiments, when the sample is utilized in vivo in subsequent applications, in some aspects, the sample is first contacted with autologous biological fluids or materials from the host prior to implantation into the same, verifying the observed enhanced fluid uptake phenotype as herein described.

In other embodiments the substrate may be a mixture of several marine originated materials or a mixture of bone and coral granules or cartilage and coral granules. In some embodiments, the solid substrate may be a composite material comprised of multiple samples of the marine organism skeletal derivatives as herein described.

In one embodiment of this invention, the solid substrate may be isolated marine organism skeletal derivative material alone, or in some embodiment, the substrate may further comprise an additional material.

In some embodiments, such additional material may include a polymer.

The term "polymer" refers, in some embodiments, to the presence of a layer of polymeric material in association with at least a portion of the solid substrate material. In some embodiments, such polymer layer is a coating for the solid substrate material.

In some embodiments, such coating may be over the entirety of the solid substrate, and in some embodiments, such coating may penetrate to within the voids and/or pores and/or hollows of the solid substrate. In some embodiments, such coating may be selectively applied to a particular region of the solid substrate, such that it creates a separate phase on the solid substrate, and in some embodiments, such polymer may be so applied that a thick polymer layer or phase is associated with a portion of a solid substrate, thereby creating a separate polymer phase in association with the solid substrate as herein described.

In one embodiment, the polymer coating provides added features to the solid substrates as herein described, for example, added tensile strength, added flexibility and/or reduced brittleness to the solid substrate.

In one embodiment of this invention, a polymer coating is permeable. In one embodiment, the permeable polymer coating comprises a special porous membrane. In one embodiment, the term "permeable" refers to having pores and openings. In one embodiment, the permeable polymer coating of this invention has pores and openings which allow entry of nutrients, a therapeutic compound, a cell population, a chelator, or a combination thereof. In one embodiment, the permeable polymer coating of this invention has pores and openings which allow exit/release of nutrients, a therapeutic compound, a cell population, a chelator, or a combination thereof.

In one embodiment, a polymer coating of this invention is discontinuous. In one embodiment, a region or a plurality of sub-regions of the coral of this invention comprise an absence of polymer coating, allowing direct contact between the coral and the environment.

In some embodiments, the solid substrate incorporates a biocompatible polymer therewithin, which is associated with the aragonite or calcite component, via any physical or chemical association. In some embodiments, the polymer is a part of a hydrogel, which is incorporated in the solid substrates of this invention. In some embodiments, such hydrogel-containing solid substrates may thereafter be lyophilized or dessicated, and may thereafter be reconstituted.

In some embodiments of the solid substrates of this invention, the polymer may be applied to the solid substrate so as to form a separate phase, or in some embodiments, the polymer may be applied as a layer onto the solid substrate, or in some embodiments, the solid substrate may comprise both polymer as an internal or externally associated layer with a separate phase attached thereto comprising the same or a different polymeric material. In some embodiments, the marine organism skeletal derivative-based solid material comprises a biocompatible polymer attached to an outer surface of the substrate.

In one embodiment, a polymer coating of this invention comprises a natural polymer comprising, collagen, fibrin, elastin, silk, hyaluronic acid, sodium hyaluronate, cross linked hyalronic acid, chitosan, cross linked chitosan, alginate, calcium alginate, cross linked calcium alginate and any combinations thereof.

In one embodiment, the polymer comprises synthetically modified natural polymers, and may include cellulose derivatives such as alkyl celluloses, hydroxyalkyl celluloses, cellulose ethers, cellulose esters and nitrocelluloses. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate and cellulose sulfate sodium salt.

In one embodiment, of this invention, a polymer comprises a synthetic biodegradable polymer. In one embodiment of this invention, a synthetic biodegradable polymer comprises alpha-hydroxy acids including poly-lactic acid, polyglycolic acid, enantioners thereof, co-polymers thereof, polyorthoesters, and combinations thereof.

In one embodiment, a polymer of this invention comprises a poly(cianoacrylate), poly(alkyl-cianoacrylate), poly (ketal), poly(caprolactone), poly(acetal), poly(α-hydroxy-ester), poly(α-hydroxy-ester), poly(hydroxyl-alkanoate), poly(propylene-fumarate), poly(imino-carbonate), poly(ester), poly(ethers), poly(carbonates), poly(amide), poly(siloxane), poly(silane), poly(sulfide), poly(imides), poly(urea), poly(amide-enamine), poly(organic acid), poly (electrolytes), poly(p-dioxanone), poly(olefin), poloxamer, inorganic or organomatallic polymers, elastomer, or any of their derivatives, or a copolymer obtained by a combination thereof.

In one embodiment, a polymer of this invention comprises poly(D,L-lactide-co-glycolide) (PLGA). In another embodiment, the polymer comprises poly(D,L-lactide) (PLA). In another embodiment, the polymer comprises poly(D,L-glycolide) (PGA). In one embodiment, the polymer comprises a glycosaminoglycan.

In one embodiment, the polymer comprises synthetic degradable polymers, which may include, but are not limited to polyhydroxy acids, such as poly(lactide)s, poly(glycolide)s and copolymers thereof; poly(ethylene terephthalate); poly(hydroxybutyric acid); poly(hydroxyvaleric acid); poly[lactide-co-($\epsilon$-caprolactone)]; poly[glycolide-co($\epsilon$-caprolactone)]; poly(carbonate)s, poly(pseudo amino acids); poly(amino acids); poly(hydroxyalkanoate)s; poly(anhydrides); poly(ortho ester)s; and blends and copolymers thereof.

In one embodiment of this invention, a polymer comprises proteins such as zein, modified zein, casein, gelatin, gluten, serum albumin, collagen, actin, α-fetoprotein, globulin, macroglobulin, cohesin, laminin, fibronectin, fibrinogen, osteocalcin, osteopontin, osteoprotegerin, or others, as will be appreciated by one skilled in the art. In another embodiment, a polymer may comprise cyclic sugars, cyclodextrins, synthetic derivatives of cyclodextrins, glycolipids, glycosaminoglycans, oligosaccharide, polysaccharides such as alginate, carrageenan ($\chi$, $\lambda$, $\mu$, $\kappa$), chitosane, celluloses, condroitin sulfate, curdlan, dextrans, elsinan, furcellran, galactomannan, gellan, glycogen, arabic gum, hemicellulose, inulin, karaya gum, levan, pectin, pollulan, pullulane, prophyran, scleroglucan, starch, tragacanth gum, welan, xanthan, xylan, xyloglucan, hyaluronic acid, chitin, or a poly(3-hydroxyalkanoate)s, such as poly(β-hydroxybutyrate), poly(3-hydroxyoctanoate) or poly(3-hydroxyfatty acids), or any combination thereof.

In one embodiment, the polymer comprises a bioerodible polymer such as poly(lactide-co-glycolide)s, poly(anhydride)s, and poly(orthoester)s, which have carboxylic groups exposed on the external surface as the smooth surface of the polymer erodes, which may also be used. In one embodiment, the polymer contains labile bonds, such as polyanhydrides and polyesters.

In one embodiment, a polymer may comprise chemical derivatives thereof (substitutions, additions, and elimination of chemical groups, for example, alkyl, alkylene, hydroxylations, oxidations, and other modifications routinely made by those skilled in the art), blends of, e.g. proteins or carbohydrates alone or in combination with synthetic polymers.

In one embodiment of this invention, the polymer is biodegradable. In one embodiment, the term "biodegradable" or grammatical forms thereof, refers to a material of this invention, which is degraded in the biological environment of the subject in which it is found. In one embodiment, the biodegradable material undergoes degradation, during which, acidic products, or in another embodiment, basic products are released. In one embodiment, bio-degradation involves the degradation of a material into its component subunits, via, for example, digestion, by a biochemical process. In one embodiment, biodegradation may involve cleavage of bonds (whether covalent or otherwise), for example in a polymer backbone of this invention. In another embodiment, biodegradation may involve cleavage of a bond (whether covalent or otherwise) internal to a side-chain or one that connects a side chain to, for example a polymer backbone.

In one embodiment, a coral of this invention is covalently associated with the polymer coating via the use of a cross-linking agent. In one embodiment, the phrase "cross-linking agent" refers to an agent which facilitates the formation of a covalent bond between 2 atoms. In one embodiment, the cross-linking agent is a zero-length cross-linking agent.

In one embodiment, the cross-linking agent is (1 ethyl 3-(3dimethyl aminopropyl)carbodiimide (EDAC), N-Sulfo-hydroxy succinamide (Sulfo NHS), 5-iodopyrimidines, N-carbalkoxydihydroquinolines, pynoloquinolinequinones, genipin or a combination thereof.

In one embodiment, the cross-linking agent is a homobi-functional cross-linker, such as, for example, a N-hydroxy-succinimide ester (e.g. disuccinimidyl suberate or dithiobis (succinimidylpropionate), homobifunctional imidoester (e.g. dimethyladipimidate or dimethyl pimelimidate), sulf-hydryl-reactive crosslinker (e.g. 1,4-di-[3'-(2'-pyridyldithio) propionamido]butane), difluorobenzene derivative (e.g. 1,5-difluoro-2,4-dinitrobenzene), aldehyde (e.g. formaldehyde, glutaraldehyde), bis-epoxide (e.g. 1,4-butanediol diglycidyl ether), hydrazide (e.g. adipic acid dihydrazide), bis-diazo-nium derivative (e.g. o-tolidine), bis-alkylhalide, or a combination thereof.

In one embodiment, the cross-linking agent is a hetero-bifunctional cross-linker, such as, for example, an amine-reactive and sulfhydryl-reactive crosslinker (e.g. N-succin-imidyl 3-(2-pyridyldithio)propionate, a carbonyl-reactive and sulfhydryl-reactive crosslinker (e.g. 4-(4-N-maleimi-dophenyl)butyric acid hydrazide), or a combination thereof.

In some embodiments, the cross-linking agent is a tri-functional cross-linkers, such as, for example, 4-azido-2-nitrophenylbiocytin-4-nitrophenyl ester, sulfosuccinimidyl-2-[6-biotinamido]-2-(p-azidobenzamido)hexanoamido] ethyl-1,3'-dithiopropionate (sulfo-SBED), or a combination thereof.

In another embodiment, the cross-linking agent is an enzyme. In one embodiment of this invention, the cross-linking agent comprises a transglutaminase, a peroxidase, a xanthine oxidase, a polymerase, or a ligase, or a combination thereof.

The choice of concentration of the cross-linking agent utilized for activity will vary, as a function of the volume, agent and polymer chosen, in a given application, as will be appreciated by one skilled in the art.

In one embodiment, the association of a coral of this invention with a polymer coating of this invention comprises a physical and/or mechanical association. For example, in one embodiment, a physical and/or mechanical association may comprise imbibing of any means, air drying, using a cross-linking agent, applying of heat, applying vacuum, applying lyophilizing methods, freezing, applying mechanical forces or any combination thereof, to promote the physical association between a coral and a polymer coating as described herein.

In some embodiments, the choice of polymer, or application of polymer to a solid substrate as herein described may be so chosen, for an added ability to prevent fluid uptake. Similarly, the surface of the solid substrate may be treated to increase fluid uptake therewithin, as well. In some embodiments, such surface treatment may include application of plasma to the solid substrate.

It will be apparent to one skilled in the art that the physical and/or chemical properties of a polymer application to a solid substrate of this invention and components thereof may influence methods of use of this invention and kits thereof, as herein described.

In one embodiment, the polymer as applied to the solid substrates of this invention has a thickness of between 2.0 µm and 0.1 µm. In one embodiment, the polymer coating has a thickness of about 1.0 µm. In one embodiment, the polymer coating of this invention has a thickness of between 10 µm and 50 µm. In one embodiment, the polymer coating as applied to the solid substrates of this invention has a thickness of about 10-25, or about 15-30, or about 25-50 µm. In one embodiment, the polymer coating as applied to the solid substrates of this invention has a thickness of about 0.0001-0.1 µm. In one embodiment, the polymer coating as applied to the solid substrates of this invention has a thickness of about 20-200 µm. In one embodiment, the polymer coating as applied to the solid substrates of this invention has a thickness of about 100-1500 µm.

In some embodiments, the polymer as applied to the solid substrates of this invention is a thin coating, which is associated with the solid substrates of this invention and has a thickness as indicated hereinabove.

In some embodiments, the polymer as applied to the solid substrates of this invention is applied throughout the solid substrates of this invention, such that, in some embodiments, the pores and voids within the solid substrates of the invention may be filled with polymers as herein described, and such polymer layer as applied may have a thickness of about 60-900 µm.

In some embodiments, the polymer as applied to the solid substrates of this invention is to a terminus or a portion of the coating forming an additional polymer phase on the solid substrates of the invention. According to this aspect, and in some embodiments, the polymer layer as applied will have a thickness of between about 0.1-10 mm.

In some embodiments, multiple solid substrates comprising polymeric additives are implanted into a desired implantation site, wherein the polymer thickness applied to a first solid substrate may vary as compared to a polymer thickness as applied to a second solid substrate, implanted in the desired site. Variations in such thickness may reflect the range described herein.

In one embodiment, the thickness of the polymer as applied to the solid substrates of this invention influences physical characteristics of a solid substrate of this invention. For example, the thickness of a polymeric application may influence elasticity, tensile strength, adhesiveness, or retentiveness, or any combination thereof of a solid substrate of this invention. In one embodiment, the polymer application increases the elasticity of a solid substrate of this invention. In one embodiment, a polymeric application increases the tensile strength of a solid substrate of this invention. In one embodiment, a polymeric application decreases the adhesiveness of a solid substrate of this invention. One skilled in the art will recognize that a polymeric application may increase adhesiveness for an item while decreasing adhesiveness for another item. For example, in one embodiment, the polymeric application increases adhesiveness for a desired compound for release and decreases adhesiveness of an invading immune cell.

Incorporation of a biocompatible polymer such as hyaluronic acid within a solid substrate of this invention, may be accomplished via any means, including, in some embodiments, pressure-driven application, for example, via application under vacuum, centrifugal force or mechanical pressure. In some embodiments, gravitational force is sufficient to allow appropriate and relatively homogenous penetration of the hyaluronic acid to a desired depth of the implant. According to this aspect, in one embodiment, visual inspection of the implant, for example using the staining with Fast Green/Safranin O, demonstrates uniform distribution of the hyaluronic acid through the substrate to a desired depth as a function of the time and conditions of application.

In one embodiment, the solid substrates of this invention may further comprise an effector compound, which in some embodiments, may be associated directly with the solid substrates of this invention, or in some embodiments, may be associated with a polymer, and applied in connection therewith.

In one embodiment, the effector compound comprises a component of a kit of this invention for use for incorporation into a solid substrate of this invention as herein described.

In one embodiment of this invention, the effector compound comprises a cytokine, a bone morphogenetic protein (BMP), growth factors, a chelator, a cell population, a therapeutic compound, or an antibiotic, or any combination thereof. In one embodiment of this invention, the marine organism skeletal derivative-based solid material further comprises cytokine, a growth factor, a therapeutic compound, a drug, metal ion, metal hydride, metal oxide or any combination thereof.

In one embodiment of this invention the effector compound might be composed of silver ions, or copper ions or other metals. In another embodiment release of this compound might be facilitated by the application of electrical charge. In another embodiment one coral might be coated with a metal such as silver and the other with a second metal such as gold. Application of electrical field or actuation by battery might cause an electrical charge to flow between the coral fragments and lead to sterilization of the area due to discharge of silver ions. Such implementation might be used to treat osteomyelitis.

In another embodiment such implementation might help induce bone formation as for example in cases of periodontitis to regenerate bone loss by either external force application or battery actuation of electrical current. Such slivers might be bone derived, ivory derived or any crustacean and marine organism.

In one embodiment of this invention, the phrase "a therapeutic compound" refers to a peptide, a protein or a nucleic acid, or a combination thereof. In another embodiment, the therapeutic compound is an antibacterial, antiviral, antifungal or antiparasitic compound. In another embodiment, the therapeutic compound has cytotoxic or anti-cancer activity. In another embodiment, the therapeutic compound is an enzyme, a receptor, a channel protein, a hormone, a cytokine or a growth factor. In another embodiment, the therapeutic compound is immunostimulatory. In another embodiment, the therapeutic compound inhibits inflammatory or immune responses. In one embodiment, the therapeutic compound comprises a pro-angiogenic factor.

In one embodiment, the effector compound comprises, an anti-helminth, an antihistamine, an immunomodulatory, an anticoagulant, a surfactant, an antibody, a beta-adrenergic receptor inhibitor, a calcium channel blocker, an ace inhibitor, a growth factor, a hormone, a DNA, an siRNA, or a vector or any combination thereof.

In one embodiment, the phrase "effector compound" refers to any agent or compound, which has a specific purpose or application which is useful in the treatment, prevention, inhibition, suppression, delay or reduction of incidence of infection, a disease, a disorder, or a condition, when applied to the solid substrates, kits and/or methods of this invention. An effector compound of this invention, in one embodiment, will produce a desired effect which is exclusive to the ability to image the compound. In some embodiments, the effector compound may be useful in imaging a site at which the compound is present, however, such ability is secondary to the purpose or choice of use of the compound.

In one embodiment of this invention, term "effector compound" is to be understood to include the terms "drug" and "agent", as well, when referred to herein, and represents a molecule whose incorporation within the solid substrate and/or kits of this invention, or whose use thereof, is desired. In one embodiment, the agent is incorporated directly within a solid substrate, and/or kit of this invention. In another embodiment, the agent is incorporated within a solid substrate and/or kit of this invention, either by physical interaction with a polymer coating, a coral, or coral particles of this invention, and/or a kit of this invention, or association thereto.

In one embodiment, the "effector compound" is a therapeutic compound.

In one embodiment, the phrase "a therapeutic compound", refers to a molecule, which when provided to a subject in need, provides a beneficial effect. In some cases, the molecule is therapeutic in that it functions to replace an absence or diminished presence of such a molecule in a subject. In one embodiment, the molecule is a nucleic acid coding for the expression of a protein is absent, such as in cases of an endogenous null mutant being compensated for by expression of the foreign protein. In other embodiments, the endogenous protein is mutated, and produces a non-functional protein, compensated for by the expression of a heterologous functional protein. In other embodiments, expression of a heterologous protein is additive to low endogenous levels, resulting in cumulative enhanced expression of a given protein. In other embodiments, the molecule stimulates a signaling cascade that provides for expression, or secretion, or others of a critical element for cellular or host functioning.

In another embodiment, the therapeutic compound may be natural or non-natural insulins, amylases, proteases, lipases, kinases, phosphatases, glycosyl transferases, trypsinogen, chymotrypsinogen, carboxypeptidases, hormones, ribonucleases, deoxyribonucleases, triacylglycerol lipase, phospholipase A2, elastases, amylases, blood clotting factors, UDP glucuronyl transferases, ornithine transcarbamoylases, cytochrome p450 enzymes, adenosine deaminases, serum thymic factors, thymic humoral factors, thymopoietins, growth hormones, somatomedins, costimulatory factors, antibodies, colony stimulating factors, erythropoietin, epidermal growth factors, hepatic erythropoietic factors (hepatopoietin), liver-cell growth factors, interleukins, interferons, negative growth factors, fibroblast growth factors, transforming growth factors of the α family, transforming growth factors of the β family, gastrins, secretins, cholecystokinins, somatostatins, serotonins, substance P, transcription factors or combinations thereof.

In any of the embodiments herein, with regard to the solid substrates as herein described, it will be appreciated that the solid substrates may serve as a local depot for sustained compound/drug release, which promotes ideal delivery and minimal degradation of the delivered material. In some embodiments, the solid substrates as herein described, may even serve as cell or tissue depots, or means of preventing immune or other cell attack, thereby extending the lifespan of such encased/protected cells and increasing production of any secreted products therefrom, for example, when pancreatic beta cells are thus encased, providing for sustained release of insulin therefrom, while preventing immune cell attack of such cells.

In any of the embodiments herein, coralline solid substrates, and their use in the methods of the present invention may further comprise, or be implanted with, other compounds such as, for example, antioxidants, growth factors, cytokines, antibiotics, anti-inflammatories, immunosuppressors, preservative, pain medication, other therapeutics, and excipient agents. In one embodiment, examples of growth factors that may be administered in addition to the HMG-CoA reductase inhibitor include, but are not limited to, epidermal growth factor (EGF), transforming growth factor-alpha (TGF-α), transforming growth factor-beta (TGF-β), human endothelial cell growth factor (ECGF), granulocyte macrophage colony stimulating factor (GM-CSF), bone morphogenetic protein (BMP), nerve growth factor (NGF), vascular endothelial growth factor (VEGF), fibroblast growth factor (FGF), insulin-like growth factor (IGF), cartilage derived morphogenetic protein (CDMP), platelet derived growth factor (PDGF), or any combinations thereof. Examples of antibiotics include antimicrobials and antibacterials.

In one embodiment, effector compounds for use in a solid substrate and/or a kit of this invention and/or a method of this invention may comprise, inter-alia, an antibody or antibody fragment, a peptide, an oligonucleotide, a ligand for a biological target, an immunoconjugate, a chemomimetic functional group, a glycolipid, a labelling agent, an enzyme, a metal ion chelate, an enzyme cofactor, a cytotoxic compound, a bactericidal compound, a bacteriostatic compound, a fungicidal compound, a fungistatic compound, a chemotherapeutic, a growth factor, a hormone, a cytokine, a toxin, a prodrug, an antimetabolite, a microtubule inhibitor, a radioactive material, or a targeting moiety, or any combination thereof.

In one embodiment, the solid substrates and/or kits of this invention and/or methods of this invention comprise or make use of an oligonucleotide, a nucleic acid, or a vector. In some embodiments, the term "oligonucleotide" is interchangeable with the term "nucleic acid", and may refer to a molecule, which may include, but is not limited to, prokaryotic sequences, eukaryotic mRNA, cDNA from eukaryotic mRNA, genomic DNA sequences from eukaryotic (e.g., mammalian) DNA, and even synthetic DNA sequences. The term also refers to sequences that include any of the known base analogs of DNA and RNA.

The solid substrates and/or kits of this invention and/or methods of use of this invention may comprise nucleic acids, in one embodiment, or in another embodiment, the solid substrates and/or kits of this invention and/or methods of use of this invention may include delivery of the same, as a part of a particular vector. In one embodiment, polynucleotide segments encoding sequences of interest can be ligated into commercially available expression vector systems suitable for transducing/transforming mammalian cells and for directing the expression of recombinant products within the transduced cells. It will be appreciated that such commercially available vector systems can easily be modified via commonly used recombinant techniques in order to replace, duplicate or mutate existing promoter or enhancer sequences and/or introduce any additional polynucleotide sequences such as for example, sequences encoding additional selection markers or sequences encoding reporter polypeptides.

In one embodiment, effector compounds for use in a solid substrate and/or a kit of this invention and/or a method of this invention may comprise, inter-alia, a cytokine, growth factor, a chelator, a cell population, a therapeutic compound, anti-cancer compound, an anti-inflammatory compound, an anti-angiogenic compound or an antibiotic, or any combination thereof.

In some embodiments, the solid substrates of this invention may comprise cells, cell populations or tissue and in some embodiments, such cells, cell populations or tissue are located internally within such solid substrate structure.

In some embodiments, the cells or tissue comprise stem or progenitor cells, or a combination thereof.

In one embodiment, effector compounds for use in a solid substrate and/or a kit of this invention and/or a method of this invention may comprise, inter-alia, a cytokine, a bone morphogenetic protein (BMP), growth factor, a chelator, a cell population, a therapeutic compound, an anti-inflammatory compound, a pro-angiogenic compound or an antibiotic, or any combination thereof.

In some embodiments, the kits and/or marine organism skeletal derivative-based solid substrates of this invention comprise known osteoinductive materials, bone cements, bone glasses, or bone fillers or a combination thereof.

In some embodiments, the bone cements may include any known cement, including β-Tricalcium phosphate, Monocalcium phosphate monohydrate (MCPM) (Ca(H2PO4) 2H2O) and mixtures thereof, including Brucite cement. In some embodiments, the cement may include amorphous calcium phosphate (ACP), dicalcium phosphate dihydrate (DCPD), dicalcium phosphate anhydrous (DCPA), α-tricalcium phosphate (α-TCP), dicalcium phosphate (DCP), tetracalcium phosphate (TTCP), monocalcium phosphate monohydrate (MCPM), calcium carbonate (CC) and others, and mixtures thereof.

In some embodiments, the kits and/or marine organism skeletal derivative-based solid substrates of this invention comprise known, and in some embodiments, commercially available osteoinductive materials, including, for example, bioactive glasses, bone cement components such as β-TCP, poly(-methyl methacrylate).

In some embodiments, the solid substrates of this invention may be seeded with cells, cell populations or tissue or in some embodiments, cells, cell populations or tissue may grow proximally, but not adherent to the solid substrates of this invention. In still other embodiments, the cells, cell populations or tissue may form tightly apposed structures in proximity to or surrounding a solid substrate as herein described.

In some embodiments, the cells or tissue comprise stem or progenitor cells, or a combination thereof.

In one embodiment of this invention, the cells or tissue as used in accordance with the substrates, methods of use or kits of this invention, are engineered to express a desired product.

In one embodiment, the phrase "a cell population" refers to a transfected cell population, a transduced cell population, a transformed cell population, or a cell population isolated from a subject, or a combination thereof. In some embodiments, transfected, transduced or transformed cells, may be seeded on the solid substrate, or in some embodiments, may be incorporated into a polymeric application thereto, or a combination thereof.

In one embodiment, a cell population of this invention comprises mesenchymal stem cells. In one embodiment, the mesenchymal stem cells are transformed.

In one embodiment, a cell population comprises cells beneficial when implanted within a subject, wherein such a solid substrate of this invention preserves the integrity or prevents rejection os such implanted cells within said substrate.

In one embodiment, the solid substrate of this invention incorporates stem or progenitor or precursor cells. Such cells can be obtained directly from a mammalian donor, e.g., a patient's own cells, from a culture of cells from a donor, or from established cell culture lines. In some embodiments, the mammal is a mouse, rat, rabbit, guinea pig, hamster, cow, pig, horse, goat, sheep, dog, cat, monkey, ape or a human. Cells of the same species and/or of the same immunological profile can be obtained by biopsy, either from the patient or a close relative. Using standard cell culture techniques and conditions, the cells are then grown in culture until confluent and used when needed. The cells may be cultured until a sufficient number of cells have been obtained for a particular application.

In some embodiments, such cells represent autografts, in that cells are cultured ex-vivo to seed the cells on the solid substrates of the invention, and such seeded solid substrates are implanted into the subject.

In some embodiments, such cells may represent allografts or xenografts, which may be incorporated within the solid substrates of this invention and implanted within a site of repair.

In one embodiment, a solid substrate of this invention comprises a cell population from in vitro culture of the coral for a time period sufficient to incorporate the cells within the coral, for example, within an internal region of such substrate.

In some embodiments, the solid substrates of this invention may be ground and prepared as a coating for a substrate or organ or tissue surface, whereby such coating prevents vascularization of associated structures located proximally thereto.

In some embodiments such ground up substrate coating may be contained within a polymer, or may be further coated by a polymer coating.

In some embodiments, such ground up substrate may be compacted, and optionally other agents are added thereto, in order to create a shapeable body comprising such ground up substrate.

In yet another embodiment the marine derived skeletal material may comprise a layer on or be otherwise attached to a metal or polymer base such as, for example titanium mesh.

Materials and methods of decreasing angiogenesis according to the invention can serve as an effective therapy for such disorders as diabetic retinopathy. Diabetic retinopathy is a major public health problem and it remains the leading cause of blindness in people between 20 and 65 years of age. Like other blinding diseases, diabetic retinopathy is related to an aberrant angiogenic response (reviewed in Garnder et al., Surv. Ophthalmol. 47 (suppl. 2):S253-262, 2002; and Spranger and Pfeiffer, Exp. Clin. Endocrinol. Diabetes 109 (suppl. 2):S438-450, 2001). In one example of a method of treating diabetic retinopathy, ground solid substrates as described herein are administered to a site proximal to the site of pathologic angiogensis in a patient, resulting in prevention of angiogenesis.

In other embodiments, the materials and kits of the invention may be useful for treating and preventing cancerous tumor growth by restricting blood supply. Uncontrolled endothelial cell proliferation is observed in tumor neovascularization and in angioproliferative diseases. Cancerous tumors cannot grow beyond a limited mass unless a new blood supply is provided. Control of the neovascularization process, therefore, represents a therapeutic modality for malignant tumors. Solid-tumor cancers that may be treated using materials and methods of the invention include gliomas, colorectal carcinomas, ovarian and prostate cancer tumors.

Accordingly, the present invention provides methods of treating neoplastic diseases and/or disorders or symptoms thereof, which comprises implanting a solid substrate as herein described, or administering a therapeutically effective amount of a pharmaceutical composition comprising ground substrate as described herein to a subject (e.g., a mammal such as a human) Thus, one embodiment is a method of treating a subject suffering from or susceptible to a neoplastic disease, such as leukemia, or disorder or symptom thereof. The method includes the step of implanting a solid substrate as herein described, or administering a therapeutically effective amount of a pharmaceutical composition comprising ground substrate as described herein sufficient to treat the disease or disorder or symptom thereof, under conditions such that the disease or disorder is treated.

The methods herein include implanting a solid substrate as herein described, or administering a therapeutically effective amount of a pharmaceutical composition comprising ground substrate as described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise implanting a solid substrate as herein described, or administering a therapeutically effective amount of a pharmaceutical composition comprising ground substrate as described herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like).

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with neoplasia, in which within the subject has been implanted a solid substrate as herein described, or to which has been administered a therapeutically effective amount of a pharmaceutical composition comprising ground substrate as described herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

The administration of a compound for the treatment of a neoplasia may be by any suitable means that results in a concentration of the therapeutic that, combined with other components, is effective in ameliorating, reducing, or stabilizing a neoplasia. When implants are inserted or compositions administered, both may be provided in a manner that is suitable for local or systemic administration (e.g., intratumoral, parenteral, subcutaneously, intravenously, intramuscularly, or intraperitoneally) route. Pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

In other embodiments, the materials and kits of the invention may be useful for treating and preventing neoplasia. In some embodiments, the term "neoplasia" is meant to refer to any disease that is caused by or results in inappropriately high levels of cell division, inappropriately low levels of apoptosis, or both. For example, cancer is a neoplasia. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). Lymphoproliferative disorders are also considered to be proliferative diseases.

Examples of other diseases for which the materials and kits of this invention may be useful in treating include all types of cancer, ocular neovascular disease, tumor formation and metastasis in tumors, hemangioma, ulcerative colitis, Crohn's disease, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eale's disease, Bechet's disease, infections causing a retinitis or choroiditis, presumed ocular histoplasmosis, Best's disease, myopia, optic pits, Stargart's disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreoretinopathy.

In some embodiments, the materials and kits of this invention are useful in treating nerve disease and nervous system conditions, in particular, Parkinson's disease, multiple sclerosis, and other neurodegenerative diseases. According to this aspect, and in some embodiments, the solid substrates of this invention are specifically positioned at regions of desired tissue regeneration or repair, whereby the presence of the same is suitable for formation of myelin sheath, which would benefit from the presence of such solid implant, which may serve as a scaffolding for promoting growth/formation of the same.

In another embodiment, the materials and kits of this invention are useful as a surface coating, limiting undesirable tissue growth, such as, for application as a synovial shunt, a stent, a valve, including artificial or animal valves or others. In some embodiments, such materials and kits may be particularly useful in any application whereby desired direction of region specific growth is of interest. For example, and in some embodiments, in regions whereby tissue growth is desired in one direction, and not in another, it is to be understood that the materials and kits of this invention may be used in conjunction with any tissue growth promoting agent, to stimulate growth in a region where such tissue growth promoting agent is present, and to diminish the likelihood/extent of tissue growth in a region where the materials and kits of this invention are applied.

In some embodiments, the materials and kits of this invention are useful in treating a coagulation disorder, such as thrombosis, including deep vein thrombosis, Pulmonary Embolism (PE), and downstream diseases such as Heart Attack and Stroke.

In some embodiments, the materials and kits of this invention are useful in treating or preventing fibrosis. In some embodiments, such condition includes pulmonary fibrosis, cystic fibrosis, cirrhosis, endomyocardial fibrosis, mediastinal fibrosis, myelofibrosis, retroperitoneal fibrosis, progressive massive fibrosis, nephrogenic systemic fibrosis, Crohn's Disease, keloids, myocardial infarction, scleroderma/systemic sclerosis, arrthrofibrosis, adhesive capsulitis, and others, as will be appreciated by the skilled artisan.

In some embodiments, the materials and kits of this invention are useful in providing a covering material for any application in which prevention or mitigation of tissue/cell growth thereupon is desired. According to this aspect, and in some embodiments, such materials and kits are useful in promoting the growth and/or stabilization of intervertebral disks, for example, by preventing or minimizing fusion/adhesion of the disk to bone while promoting nerve cell growth, etc. In some embodiments, such covering may serve as a wound cover, providing a means for wound healing underneath such cover, while preventing invasion of pathogenic microorganisms, while permitting gas exchange at the wound site.

In some embodiments, the materials and kits of this invention are useful in providing a substrate for in vitro cell and tissue growth. In some aspects, such in vitro substrates are particularly useful for growth of stem cells, fat cells, nerve cells and tissue of the same. It will be understood by the skilled artisan that any cell growth which will benefit from provision of the materials and kits of this invention are contemplated herein and to be considered as part of this invention. In some embodiments, the solid substrate is useful as a substrate for in vitro cell and tissue growth whose growth is promoted by contact independence.

In some embodiments, uses described for any of the materials and kits of this invention are to be understood to encompass ground materials, as well, for such use.

In some embodiments, such ground materials of this invention may be used in combination with any other material, which stimulates cell and tissue growth for structures/cells which are positively impacted by vascularization and the same may serve as a composite substrate to promote tissue growth/formation of multiple cell types/origins.

In some embodiments, the materials and kits of this invention are useful in preventing calcium binding/accumulation, atherosclerosis and others.

As exemplified herein, blood, water and other hydrophilic fluids as described were applied to the coral samples and absorption of the fluid within the coral samples was assessed.

FIG. 1 depicts the results of a representative absorption studies conducted as described, showing patterns of uptake, substantial uptake and partial, minimal or no uptake of the fluid, respectively, depending upon the sample assessed. This variability in the pattern of absorption, surprisingly provided a means of selecting solid substrates with optimized efficacy in mitigating or preventing cell and tissue adherence and/or vascularization following implantation.

Example 2 as provided herein demonstrates correlation between minimal specific uptake of biological fluid within the implanted coral solid substrate and concomitant surprising structural differences from substrates with a higher specific uptake, correlating with diminished cell/tissue adherence.

Also exemplified is the development of a screening protocol established to select for such optimized coral-based solid substrate for mitigating or preventing cell or tissue growth, provided in Example 3.

This invention provides the unexpected application of optimally selected coral based solid substrates being useful in mitigating or preventing cell and tissue adherence and/or vascularization.

It will be appreciated that the solid substrates of this invention may be of any suitable shape or size to accommodate its application in accordance with the methods of this invention. For example, and in some embodiments, for applications of the solid substrates of this invention within long bones of a subject, the dimensions of the solid substrate will be scaled to approximate that of the site into which the scaffold will be implanted, and may be on an order of magnitude scaling from millimeters to centimeters, as needed. Similarly, shapes of the solid substrates of the invention may be any shape into which the solid substrates of this invention may be machined or processed, and may have any configuration as will be appropriate to achieve the desired application for cell and/or tissue growth and restored function.

It will be apparent to those skilled in the art that various modifications and variations can be made in the solid substrates, kits, process and methods of the present invention without departing from the spirit or scope of the invention.

In some embodiments, the term "comprise" or grammatical forms thereof, refers to the inclusion of the indicated components of this invention, as well as inclusion of other active agents, and pharmaceutically acceptable carriers, excipients, emollients, stabilizers, etc., as are known in the pharmaceutical industry.

In one embodiment, the term "about" refers to a variance of from 1-10%, or in another embodiment, 5-15%, or in another embodiment, up to 10%, or in another embodiment, up to 25% variance from the indicated values, except where context indicates that the variance should not result in a value exceeding 100%.

In one embodiment, the present invention provides combined preparations. In one embodiment, the term "a combined preparation" defines especially a "kit of parts" in the sense that the combination partners as defined above can be used independently or in different combinations i.e., simultaneously, concurrently, separately or sequentially.

EXAMPLES

Example 1

Physical Properties Variability in Coralline-Based Solid Substrates of this Invention Materials and Methods A diamond disk saw was used to remove an outer coral layer, and large sections from which representative smaller sections of desired dimensions were cut from the coral block.

Coral from the hydrocoral *Porites lutea* which has an average pore size of 100-150 µm was harvested from various regions within a coral. The coral was evaluated visually for its appearance, density, and porosity. Coral was then optionally immersed in 5% sodium hypochlorite for removal of external organic tissue. Briefly, coral was first exposed to a 5% sodium hypochlorite solution for 30 minutes, 3 exchanges at temperature range RT at 50° C., and subatmospheric pressure using vacuum pressure ranging from 0.2-0.00001 Bar. The coral sections were then exposed to a 10% solution of hydrogen peroxide for 15 minutes at a temperature range of from RT-50° C., and subatmospheric pressure using vacuum pressure ranging from 0.2-0.00001 Bar. The cleaned sections were then washed in distilled water for 30 minutes, 3 exchanges at a temperature range of from RT-50° C., and subatmospheric pressure using vacuum pressure ranging from 0.3-0.00001 Bar.

The coral was optionally sterilized by exposure to gamma radiation at a strength of at least 22.5 kGy and can then be stored aseptically, in packaging material, and in particular, the smaller samples were irradiated, whereas larger blocks assessed were not irradiated.

Each section was then place in a plastic petri dish and 2 ml of fluid was applied to each dish. Observations regarding absorption of the fluid were recorded. Fluids used included animal blood, plasma water and various colored solutions.

Results

To determine whether sample removal from various regions provides for materials, which vary in their physical characteristics and whether such variability provides for alternative qualities to the same, blood and other fluids listed were applied to the coral samples and absorption of the fluid within the coral samples was assessed.

FIG. 1 depicts the results of a representative absorption study conducted as described. Coral samples were isolated from different regions of a coral block, and assessed for their pattern and intensity of absorption of blood applied thereto. Surprisingly, there appears to be no uniformity in terms of the absorption profile, and the same is not an "all or none" phenomenon.

Figure 1B:
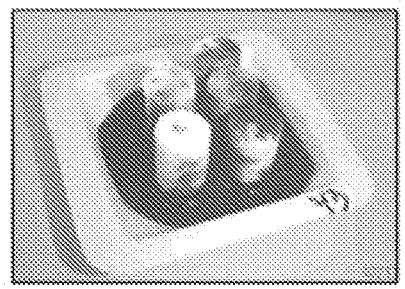
Figure 1C:
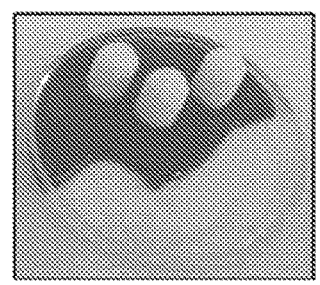
Figure 1D:
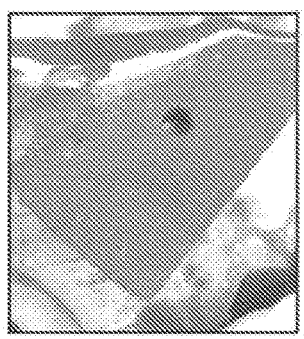
FIGS. 1D-1F show a larger block of the coral solid substrate from which the smaller implants were isolated.
Figure 1E:
Figure 1F:
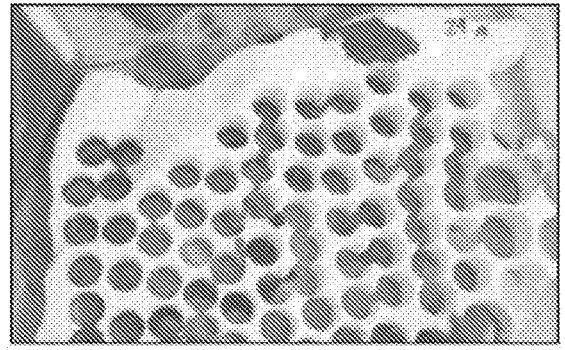

FIG. 1A for example, shows reasonably substantial absorption throughout the structure, whereas FIG. 1C shows poor to no absorption throughout, and FIG. 1B provides an interim phenomenon within the structure in that some regions substantially absorb the fluid and some regions absorb minimal to no fluid. FIGS. 1D-1F show cross-sectional slices through coral pieces from which coral plugs were cut and prepared, providing different patterns of absorption within the macrostructures, as well.

Other fluids were assessed in terms of their absorption within parallel samples comparable to the sample in FIG. 1C. To serve as a stain, a salt solution, and protein solution, carbohydrate solutions, ionic solutions were prepared and applied, and the results substantially mirrored that of the applied blood in that poor to no absorption occurred. Plain water applied thereto provided substantially the same results, resulting poor to no absorption within the coral sample.

As demonstrated herein, the size of the sample assessed is not limiting, and indeed samples of various sizes and thicknesses may be thus assessed.

Example 2

Structural Differences as a Function of Certain Physical Properties in Coralline-Based Solid Substrates of this Invention In order to assess the consequence of the phenotypic variability in blood absorption in the plugs of Example 1, coral plugs were prepared using a standard production method including three hypochlorite washes, hydrogen peroxide treatment and multiple DDW washes. Their spontaneous fluid uptake and total fluid uptake values were determined. The implants were drilled and sterilized as was previously described.

Figure 3A:
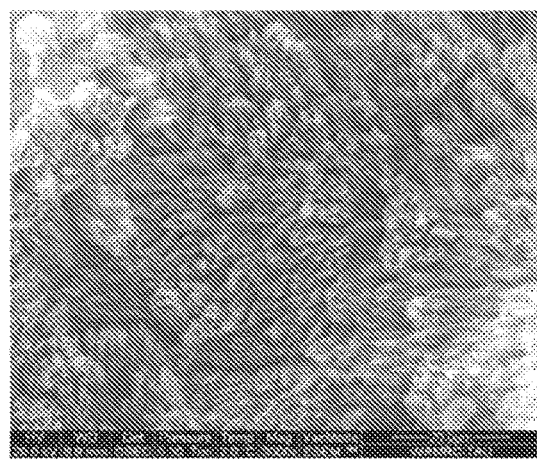
FIG. 3A reveals a surface covered by crystals sized from about 1 to 4 micron.
Figure 3B:
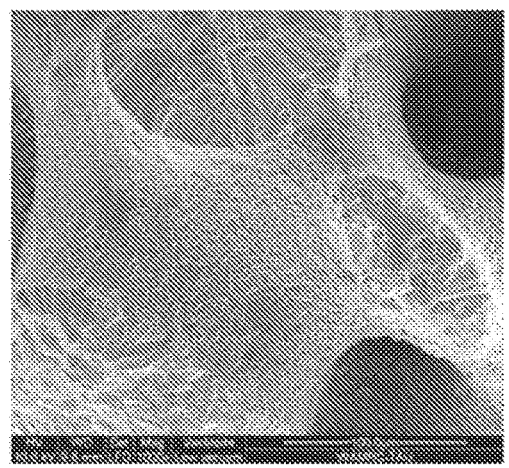
FIG. 3 demonstrates the different surface characteristics as seen by environmental scanning electron microscopy between solid substrates characterized by a specific fluid uptake capacity value of more than 75% (FIGS. 3A, 3B and 3C) versus solid substrates characterized by a specific fluid uptake capacity of less than 40% (FIGS. 3D, 3E and 3F, respectively.
FIG. 3D demonstrates a different sample characterized by low fluid uptake capacity that has poor "wetting" capabilities.
FIG. 3F, in contrast, shows a specimen characterized by low water uptake capacity demonstrating a smooth surface and no wetting under these conditions, with fluid droplets readily apparent as jutting out from the surface (see arrow).
Figure 3C:
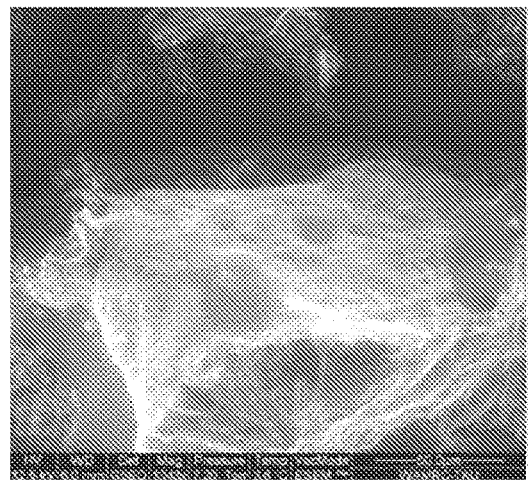
Figure 3D:
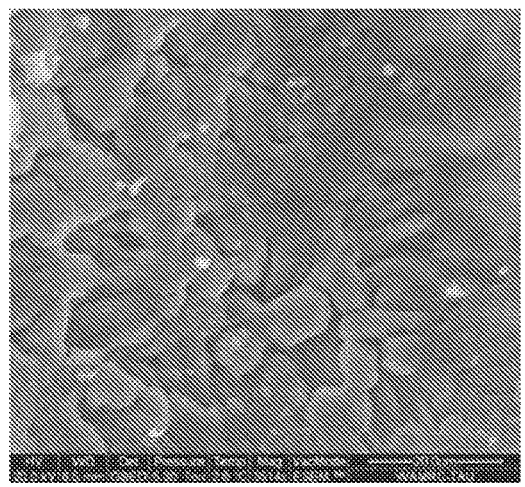
Figure 3E:
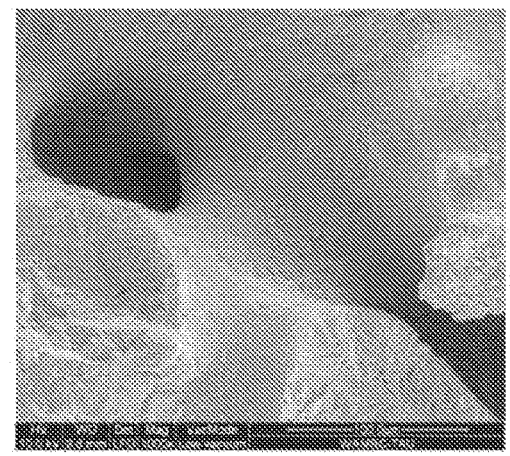
Figure 3F:
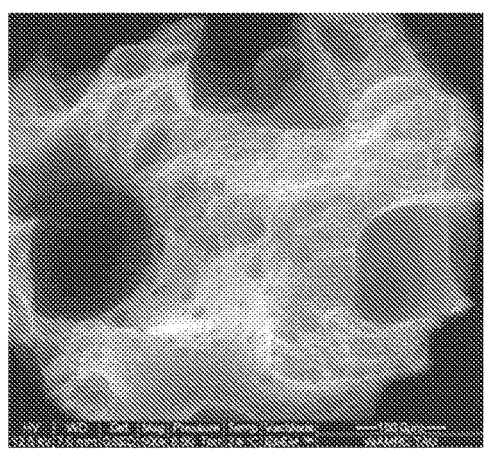

Implants were processed for environmental scanning electron microscopy according to standard methods. FIG. 3A-C demonstrate the surface structure of a solid substrate with a higher specific fluid uptake capacity value as compared to that of substrates with a lower specific fluid uptake capacity value (compare FIGS. 3A-C and 3D-F). Substrates with a lower specific fluid uptake capacity value exhibited a smoother outer surface structure, as compared to those with a higher specific fluid uptake capacity value, while the crystalline structure of the latter sample was easily seen. Furthermore, wettability tests demonstrated that water drops seen on the surface of the substrates with a lower specific fluid uptake capacity value, were characterized by a high contact angle, relative to the surface (FIG. 3F). In marked contrast, water drops seen on the surface of substrates characterized by a higher specific fluid uptake capacity value, exhibited a low contact angle relative to the surface (FIG. 3C). These data are consistent with an available surface of substrates with a lower specific fluid uptake capacity value, as being more hydrophobic, whereas substrates with a higher specific fluid uptake capacity value are more hydrophilic.

Example 3

Establishing a Screening Protocol for Coralline-Based Solid Substrates

Based on the findings in Examples 1 and 2, a screening protocol was established to select for an optimized coral-based solid substrate for mitigating or preventing cell or tissue adherence and/or vascularization. The coral sample being assessed will be dry, and in some aspects, it may be dried under vacuum and/or heated toward this end. A dry weight for each sample may be recorded. Fluid as described herein may be added to each assay container. In some embodiments, at least a 1:1 ratio or excess of the size of the sample in mm to the volume of fluid added in ml is applied to the container. The coral sample is then brought into contact with the fluid and the weight of the coral sample is assessed. A spontaneous fluid uptake value is established, based on either the complete uptake of the volume applied to the sample or based on the change in weight of the sample. Samples may optionally be dried, prior to further manipulation of the sample. A significantly increased amount of fluid is brought into contact with the sample and a vacuum is applied for a period of time to ensure maximal uptake of the applied fluid into the coral sample. A total fluid uptake capacity is assessed and the specific fluid uptake capacity value is determined. If the value is below the cutoff value of 40%, then the sample will be noted for its suitability as a solid substrate for mitigating or preventing cell or tissue adherence and/or vascularization. When the sample is utilized in vivo in subsequent applications, in some aspects, the sample is first contacted with autologous biological fluids or materials from the host prior to implantation into the same, in part in order to verify that such implant does not absorb such fluid (FIG. 2).

Example 4

Prescreening Coralline-Based Solid Substrates for Implantation

For applications in mitigating or preventing cell or tissue growth and/or vascularization, solid substrates are assessed for their ability to absorb autologous biologic fluid/materials, such as, for example, whole blood, taken from the subject prior to the implantation procedure. Substrates that provide a specific fluid uptake capacity value of less than 40% are then implanted in the desired site.

Solid substrates may be prepared according to any embodiment as described herein, as will be appreciated by the skilled artisan.

The substrates are envisioned for use in veterinary applications, as well as in the treatment of human subjects. At appropriate intervals, standard methodology is employed to assess localization of the implanted substrates within tissue, for example, X-ray, CT or MRI imaging may be performed to verify the position of the implants.

Implantation may be at any suitable location.

The diameter of the implant will be appropriate for the diameter of the implantation site being treated.

In applications relating to mitigating or preventing cell or tissue adhesion and/or vascularization, it is noted that solid substrates characterized by a specific fluid uptake capacity value of less than 40% will significantly outperform solid substrates characterized by a specific fluid uptake capacity value of more than 75%, in terms of their ability to prevent cell or tissue adherence, mitigate angiogenesis/vascularization and promote sustained delivery or diminished autorejection at the implantation site, or a combination thereof.

Example 5

Physical Properties Variability in Coralline-Based Solid Substrates of this Invention Natural surfaces are heterogenic due to their variable material composition, surface roughness and porosity and thus demonstrate variable water repellence/adhesion characteristics. Contact angle measurements can characterize the wetting of rough surfaces, taking the topography and the chemical structure of the surface into account.

Contact angle measurement was with goniometry. The contact angle is an equilibrium contact angle measured macroscopically on a solid surface. The same is to be distinguished from Young contact angles, measured on atomically smooth, chemically homogeneous surfaces.

The regions were classified into three classes and their relative surface areas were approximated as a percentage out of the total surface area:

Regions characterized by contact angles of between 0 and 60 deg, appear as white regions in the figures provided. Regions characterized by a contact angle of between 60 and 90 deg are marked in dark grey in the figures provided, and regions characterized by a contact angle of 90 deg and higher are marked in light grey in the figures provided.

Water drops of 1 ul-10 ul volume were deposited on cleaned and dried coral samples with a precise micro-dosing syringe. The contact angles were measured with a Rame-Hart goniometer (Model 500) with an accuracy of 0.1 deg (Bormashenko, 2012). Measurements were assessed for both sides of the drop and averaged. The test medium employed was physiologic saline.

Three 3×3 mm coral samples termed, R43, R34, R44 were assessed. Prior to evaluation of contact angles, the specific fluid uptake capacity value was assessed for samples from each block, and the results are presented in Table 1.

| Coral | Specimen (Name) | specific fluid uptake capacity value |
|---|---|---|
| 43 | 1 | 0.62 |
|  | 2 | 0.46 |
|  | 3 | 0.60 |
|  | 4 | 0.31 |
|  | por1 | 0.17 |
|  | por2 | 0.17 |
|  | por3 | 0.37 |
| 44 | 1 | 0.32 |
|  | 2 | 0.82 |
|  | 3 | 0.88 |
| 34 | 1 | 0.70 |
|  | 2 | 0.39 |
|  | 3 | 0.33 |

FIG. 4 provides photographs of coral sample R43 specimens evaluated for their contact angles. FIGS. 4A and 4B show regions cut from the larger block, which were assessed for their contact angle characterization. The majority of regions of the block assessed in FIGS. 4A and 4B provided for a contact angle primarily of less than 60 degrees. Certain areas in FIGS. 4C and 4D provided for a contact angle of between 60 and 90 degrees (FIG. 4C) and over 90 degrees (FIG. 4D).

Figure 4A:
FIGS. 4A and 4B show where the samples which were assessed for their contact angle characterization were cut from a larger block, and FIGS. 4C and 4D provide the contact angle values obtained for the indicated regions. The majority of regions of the block assessed in FIGS. 4A and 4B provided for a contact angle primarily of less than 60 degrees. Certain areas in FIGS. 4C and 4D provided for a contact angle of between 60 and 90 degrees (FIG. 4C) and over 90 degrees (FIG. 4D).
Figure 4B:
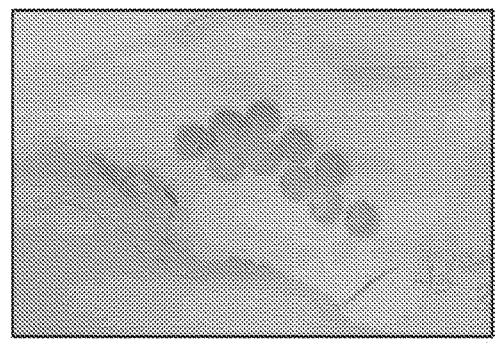
Figure 4C:
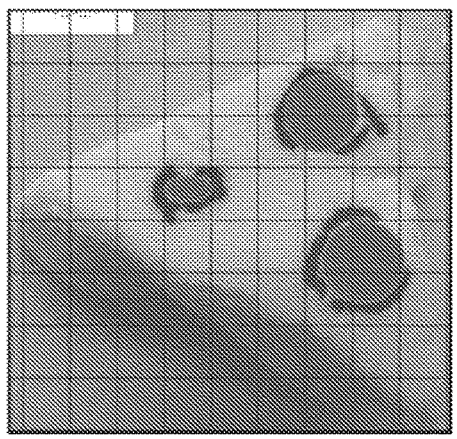
FIG. 4 provides photographs of embodied implants evaluated for their contact angle, when exposed to fluid.
Figure 4D:
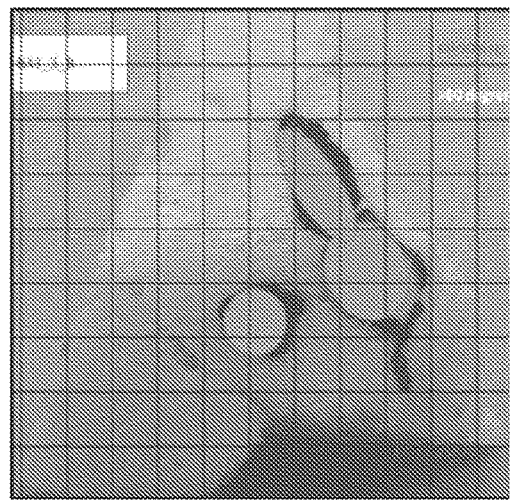
Figure 5C:
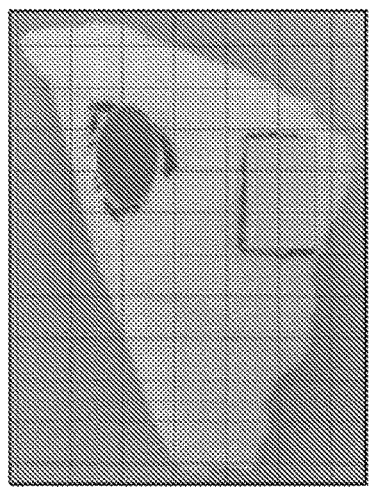
FIG. 5 photographs of embodied implants evaluated for their contact angle, when exposed to fluid.
FIG. 5A shows regions cut from the larger block, which were assessed for their contact angle characterization. The majority of regions of the block assessed in FIGS. 5B and 5C provided for a contact angle primarily of less than 60 degrees. Certain areas in FIGS. 5B and 5C provided for a contact angle of between 60 and 90 degrees and over 90 degrees (blue versus red regions, respectively).
Figure 5B:
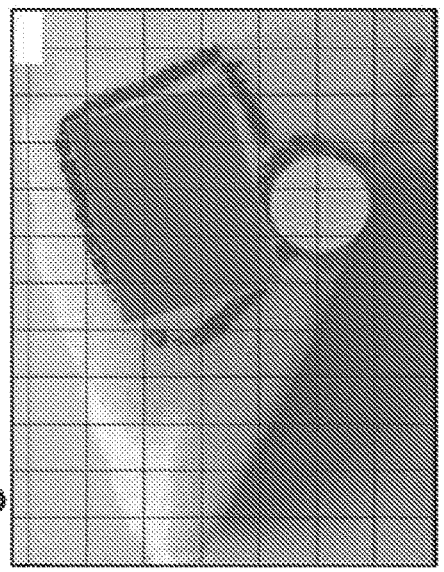
Figure 6B:
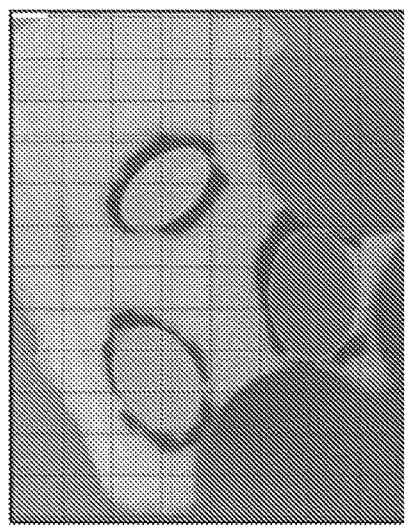
FIG. 6 similarly provides photographs of embodied implants evaluated for their contact angle, when exposed to fluid.
FIG. 6A shows regions cut from the larger block, which were assessed for their contact angle characterization. The majority of regions of the block assessed in FIG. 6B provided for a contact angle primarily of less than 60 degrees. Certain areas in FIG. 6B provided for a contact angle of between 60 and 90 degrees and over 90 degrees (blue versus red regions, respectively).
Figure 5A:
Figure 6A:
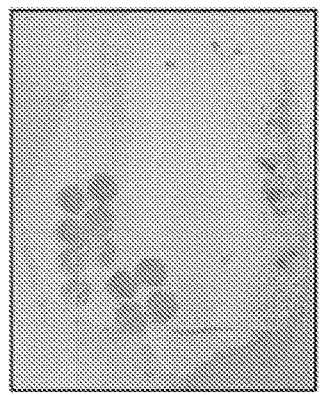

FIG. 5 provides photographs of coral sample R34 specimens evaluated for their contact angles. FIG. 5A shows regions cut from the larger block, which were assessed for their contact angle characterization. The majority of regions of the block assessed in FIGS. 5B and 5 provided for a contact angle primarily of less than 60 degrees. Certain areas in FIGS. 5B and 4C provided for a contact angle of between 60 and 90 degrees and over 90 degrees (dark grey versus light grey regions, respectively). FIG. 6 similarly provides photographs of coral sample R44 specimens evaluated for their contact angles. FIG. 6A shows regions cut from the larger block, which were assessed for their contact angle characterization. The majority of regions of the block assessed in FIG. 6B provided for a contact angle primarily of less than 60 degrees. Certain areas in FIG. 6B provided for a contact angle of between 60 and 90 degrees and over 90 degrees (dark grey versus light grey regions, respectively).

The contact angle measurements parallel the specific fluid uptake capacity values obtained for respective coral samples. Accordingly, the improved solid substrates for promoting cell or tissue growth or restored function of this function may be characterized by either a determination of a contact angle, or a specific fluid uptake capacity value.

Furthermore, environmental scanning electron microscopy (ESEM) studies confirmed the results of the contact angle studies presented herein.

Table 2 presents the specific fluid uptake capacity values for the coral samples evaluated by ESEM.

| Coral | Specimen (Name) | specific fluid uptake capacity value |
|---|---|---|
| R27 | 7 | 0.87 |
| R30 | 40 | 0.04 |
| R43 | 1 | 0.62 |

Figure 7A:
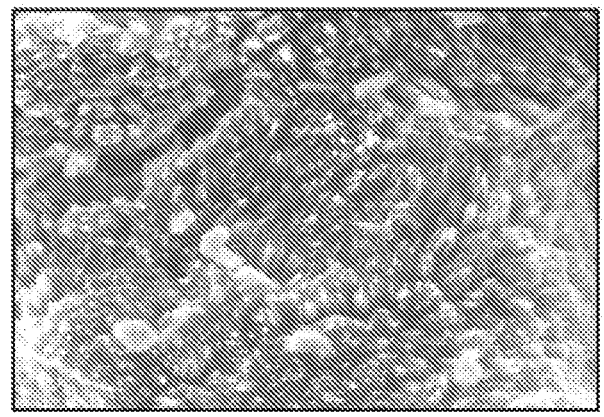
FIG. 7 demonstrates the results of ESEM analysis showing comparative surface wetting characteristics. The sample assessed in FIG. 7A showed a zero drop angle value, and no drop formation.
FIG. 7B depicts a sample, which following the application of fluid, failed to "wet" when water was applied.
FIG. 7C shows that following re-dessication, water droplets were evident on the surface, consistent with a phenotype of poor surface wetting.
Figure 7B:
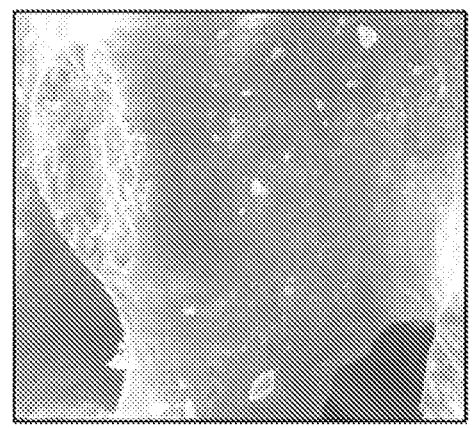
Figure 7C:
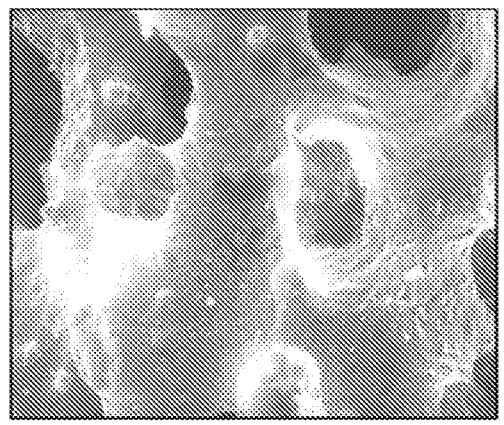

FIG. 7 presents the results of ESEM analysis conducted on the samples described in Table 2. Samples assessed from the R27-7 block provided for a zero drop angle value, and no drop formation seen (FIG. 7A). FIG. 7B-7C present the results for sample R30-40. FIG. 7B was taken following application of fluid, and it was noted that the sample failed to "wet" when water was applied. FIG. 7C shows that following re-dessication, water droplets were evident on the surface, consistent with a phenotype of poor surface wetting.

Taken together, these results are corroborative of the contact angle data, as well specific fluid uptake capacity values obtained for respective coral samples. A sample having a specific fluid uptake capacity values obtained for respective coral samples of more than 75% exhibited no drop formation on the surface, consistent with a "good wetting" phenotype (FIG. 7A), whereas samples with a lower specific fluid uptake capacity value exhibited droplet formation during dessication.

Example 6

Structural Differences as a Function of Certain Physical Properties in Coralline-Based Solid Substrates of this Invention Implants were processed for environmental scanning electron microscopy according to standard methods. FIG. 8A-C demonstrate the surface structure of a solid substrate with a higher specific fluid uptake capacity value as compared to that of substrates with a lower specific fluid uptake capacity value (compare FIGS. 8A-C and 8D-F). Substrates with a lower specific fluid uptake capacity value exhibited a smoother outer surface structure, as compared to those with a higher specific fluid uptake capacity value, while the the crystalline structure of the latter sample was easily seen. Furthermore, wettability tests demonstrated that water drops seen on the surface of the substrates with a lower specific fluid uptake capacity value, were characterized by a high contact angle, relative to the surface (FIG. 8F). In marked contrast, water drops seen on the surface of substrates characterized by a higher specific fluid uptake capacity value, exhibited a low contact angle relative to the surface (FIG. 8C). These data are consistent with an available surface of substrates with a lower specific fluid uptake capacity value, as being more hydrophobic, whereas substrates with a higher specific fluid uptake capacity value are more hydrophilic.

Figure 9D:
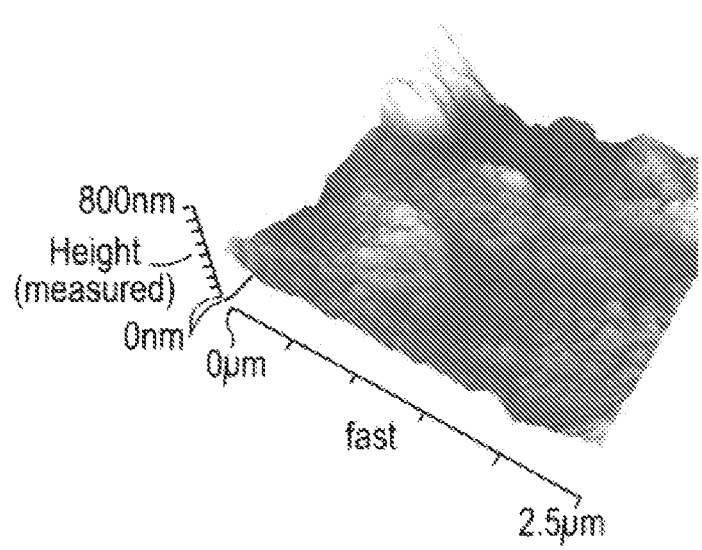
FIG. 9 demonstrates the microscopic structure as determined by AFM, of isolated substrates characterized by minimal biologic fluid uptake, versus those characterized by substantial biologic fluid uptake at various magnifications in samples with minimal biologic fluid uptake indicate a much smoother external surface as compared to samples with substantial uptake (FIGS. 9A-9C versus 9D-9F).
Figure 9E:
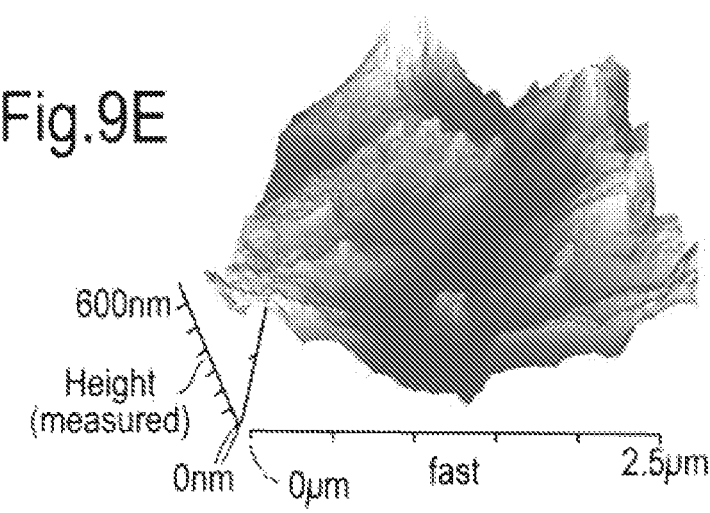
Figure 9F:
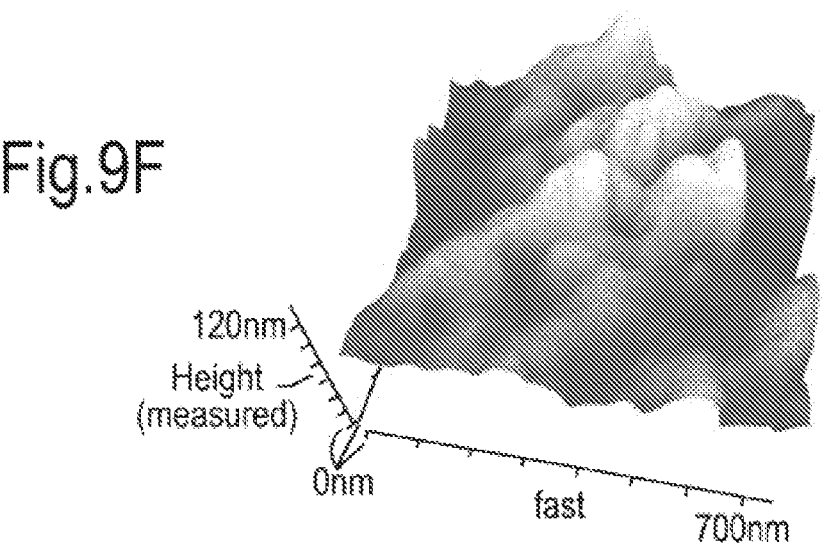

FIG. 9 demonstrates the microscopic structure as determined by AFM, of isolated substrates characterized by minimal biologic fluid uptake, versus those characterized by substantial biologic fluid uptake at various magnifications in samples with minimal biologic fluid uptake indicate a much smoother external surface as compared to samples with substantial uptake (FIGS. 9A-9C versus 9D-9F).

Example 6

Establishing a Screening Protocol for Coralline-Based Solid Substrates

Figure 10:
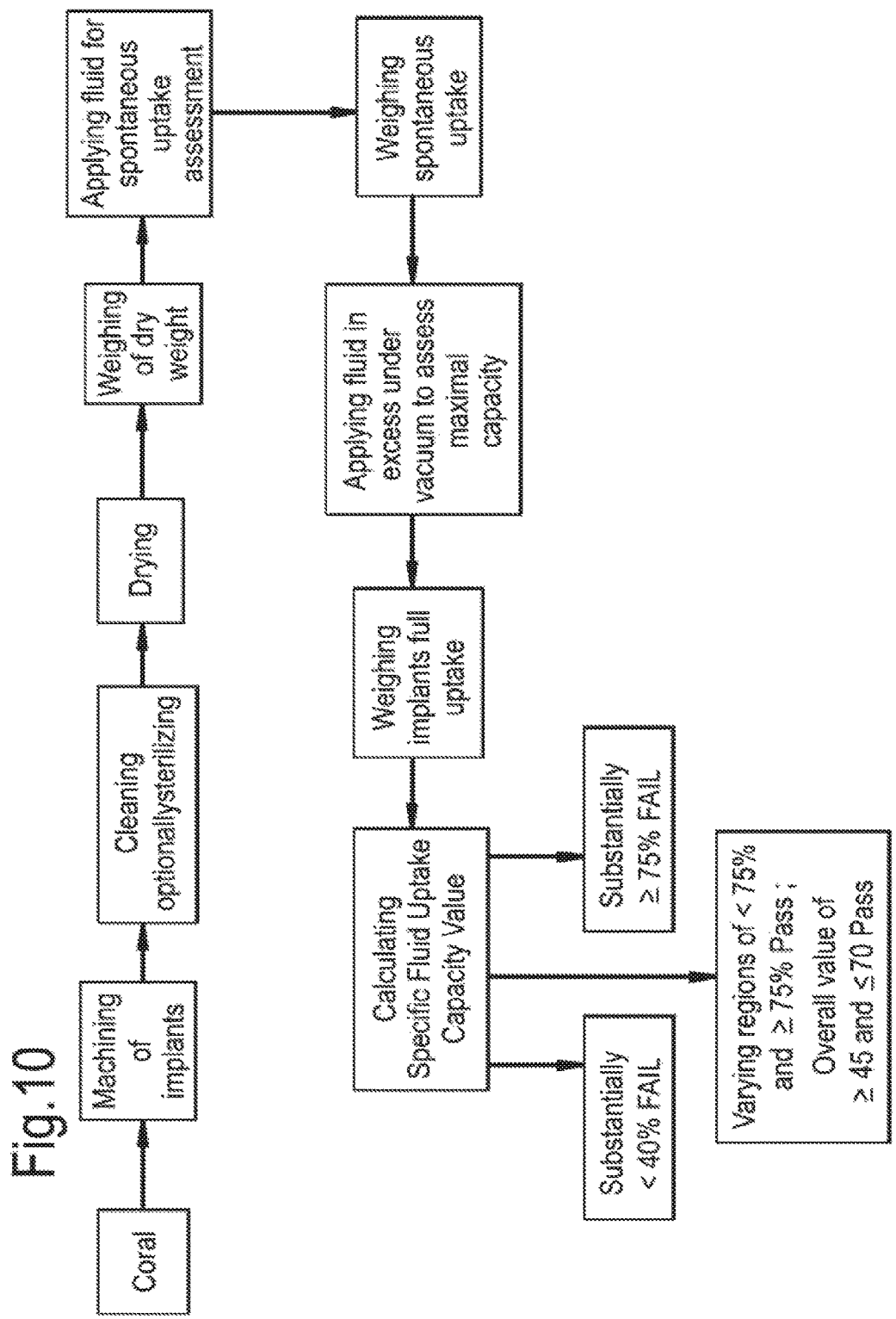
FIG. 10 presents a flow chart for an embodied screening protocol for the identification of optimized marine organism skeletal derivative-based solid substrates for promoting cell or tissue growth or restored function.

A screening protocol may be established to select for an optimized coral-based solid substrate for promoting cell or tissue growth or restored function. FIG. 10 provides a flow diagram of an envisioned screening protocol process. Coral samples are identified, isolated and machined to a desired size and shape, or assessed in blocks. The samples are then cleaned and optionally sterilized, then dried. The coral sample being assessed may be dried under vacuum and/or heated toward this end.

A dry weight for each sample may then be recorded.

Fluid as described herein is added to each assay container in an approximately 1:1 ratio or slightly more, i.e. equal to or slightly more than the size of the sample in mm as compared to the volume of fluid in ml is added to the container.

The sample may then be weighed and a spontaneous fluid uptake value is determined.

Samples may optionally be dried, prior to further manipulation of the sample.

A significantly increased amount of fluid is brought into contact with the sample and a vacuum is applied for a period of time to ensure maximal uptake of the applied fluid into the coral sample.

A total fluid uptake capacity is assessed and the specific fluid uptake capacity value is determined by dividing the spontaneous fluid uptake value by the total fluid uptake capacity.

If the value exceeds the cutoff value of 75%, then the sample will be noted for its suitability as a solid substrate for promoting cell or tissue growth or restored function. When the sample is utilized in vivo in subsequent applications, in some aspects, the sample is first contacted with autologous biological fluids or materials from the host prior to implantation into the same. If the value is less than the stated cutoff value, then the sample is not used as a solid substrate for promoting cell or tissue growth or restored function.

Example 7

Improved Solid Substrate Incorporation as a Function of Certain Physical Properties in Coralline-Based Solid Substrates of this Invention In order to assess the consequence of the phenotypic variability in blood absorption in the plugs, coral plugs are prepared using a standard production method including three hypochlorite washes, hydrogen peroxide treatment and multiple double distilled water washes. Their spontaneous fluid uptake and total fluid uptake values are determined as described in Example 6, with water being the sample fluid assessed in this case. Sample implants with an established spontaneous fluid uptake value are also checked for their spontaneous blood uptake ability.

Implants are graded as red, white, and intermediate, with intermediate referring to regions that are red and regions that remain white (FIG. 10) Implants are placed in a tissue of interest and the effects of the implant on the surrounding tissue are monitored and recorded.

Example 8

Automated Process and Apparatus for Isolating and Preparing Optimized Marine Organism Skeletal Derivative—Based Solid Substrates Coral samples of the hydrocoral *Porites lutea* are isolated as described in Example 1 and implants are prepared. The implants 20-10 are placed in the holding cassette 20-20, and the cover 20-70 is placed on the device. Negative pressure is applied via the vacuum 20-30 for a prescribed period of time, until the implants are fully dry and then the application is halted. The apparatus then individually weighs each implant to establish a dry weight. An automated cycle is initiated, which facilitates filling and a desired fluid level is maintained during the process. The cassettes 20-20 are individually raised and lowered into a first fluid level, via the cassette manipulator 20-40 within the fluid to enable spontaneous fluid uptake, and the implant manipulator 20-60 individually orients/moves the individual implants for weight determination, to determine the spontaneous fluid uptake value followed by optionally a pass of each implant past a drying/blotting station. The individual implants are all weighed and returned to their place within the cassettes. The cassettes 20-20 are then again individually raised and lowered into a second, significantly higher fluid level, via the cassette manipulator 20-40 within the excess fluid to facilitate full immersion of the implants, and negative pressure is applied again via the vacuum 20-30 for a defined period of time, ensuring maximum fluid uptake within each implant. The implant manipulator 20-60 again individually orients/moves the individual implants for a second weight determination, which provides the total fluid uptake value. The data processing unit of the apparatus determines and provides an output of the specific fluid uptake value, optionally specifically identifying which samples are to be selected based on indicated criteria.

It will be understood that the dimensions of the cassette will be constructed to accommodate implants of varying size. The apparatus can be built to scale, as well, to accommodate a larger or smaller number of cassettes, and the materials will be appropriate for the various fluids being assessed for their uptake within the stated implants. Sensors and appropriate relays are incorporated to, for example, provide a warning system in case of malfunction and the apparatus may further comprise a data processing unit, to calculate the specific fluid uptake capacity value from the determined spontaneous and total fluid uptake values obtained. Statistical analysis may also be included as part of the data processing package provided optionally with the claimed apparatuses of this invention. Specific selection of samples with the desired spontaneous fluid uptake value may also be accomplished using the automated device as herein described.

It will be understood by those skilled in the art that various changes in form and details may be made therein without departing from the spirit and scope of the invention as set forth in the appended claims Those skilled in the art will recognize, or be able to ascertain using no more than routine experimentation, many equivalents to the specific embodiments of the invention described herein. Such equivalents are intended to be encompassed in the scope of the claims.

In one embodiment of this invention, "about" refers to a quality wherein the means to satisfy a specific need is met, e.g., the size may be largely but not wholly that which is specified but it meets the specific need of cartilage repair at a site of cartilage repair. In one embodiment, "about" refers to being closely or approximate to, but not exactly. A small margin of error is present. This margin of error would not exceed plus or minus the same integer value. For instance, about 0.1 micrometers would mean no lower than 0 but no higher than 0.2. In some embodiments, the term "about" with regard to a reference value encompasses a deviation from the amount by no more than 5%, no more than 10% or no more than 20% either above or below the indicated value.

In the claims articles such as "a", "an" and "the" mean one or more than one unless indicated to the contrary or otherwise evident from the context. Claims or descriptions that include "or" or "and/or" between members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides, in various embodiments, all variations, combinations, and permutations in which one or more limitations, elements, clauses, descriptive terms, etc., from one or more of the listed claims is introduced into another claim dependent on the same base claim unless otherwise indicated or unless it would be evident to one of ordinary skill in the art that a contradiction or inconsistency would arise. Where elements are presented as lists, e.g. in Markush group format or the like, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein. Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format.

What is claimed is:

1. A process for selection of a marine organism skeletal derivative-based solid substrate optimized for mitigating or preventing cell or tissue adhesion and vascularization, said process comprising:

isolating or preparing a marine organism skeletal derivative-based solid material;

establishing a specific fluid uptake capacity value of said marine organism skeletal derivative-based solid material, which specific fluid uptake capacity value is determined by establishing a spontaneous fluid uptake value divided by a total fluid uptake value; or contacting said marine organism skeletal derivative-based solid material with a fluid and establishing a contact angle for said marine organism skeletal derivative; and selecting a marine organism skeletal derivative-based solid material characterized by a specific fluid uptake capacity value of less than 40%; or characterized by a contact angle of more than 60 degrees, when in contact with a biologic fluid or a protein-containing, salt-containing or carbohydrate containing solution.

2. The process of claim 1, wherein said marine organism skeletal derivative is comprised substantially of a coral or coral-based derivative or wherein said marine organism skeletal derivative is comprised substantially of aragonite, calcite, hydroxyapatite or a combination thereof.

3. The process of claim 2, further comprising the step of partially or fully converting a marine organism skeletal derivative-based solid material to hydroxyapatite prior to establishing said specific fluid uptake capacity value, wherein said marine organism skeletal derivative-based solid material is aragonite.

4. The process of claim 1, wherein said marine organism skeletal derivative-based solid material contains ground particles derived from coral, suspended in a biocompatible matrix; or wherein said marine organism skeletal derivative-based solid material comprises a bone graft or bone substitute material; or wherein said marine organism skeletal derivative-based solid material further comprises a bone filler.

5. The process of claim 1, wherein said marine organism skeletal derivative-based solid material can be used as a bone filler or bone substitute material.

6. The process of claim 1, wherein said process further comprises the step of contacting said marine organism skeletal derivative-based solid material with a fluid for from 0.1-15 minutes allowing for spontaneous fluid uptake of said fluid within said marine organism skeletal derivative-based solid material to arrive at said spontaneous fluid uptake value, or wherein said process further comprises the step of contacting said marine organism skeletal derivative-based solid material with a fluid for from 12 up to 24 hours allowing for spontaneous fluid uptake of said fluid within said marine organism skeletal derivative-based solid material to arrive at said spontaneous fluid uptake value.

7. The process of claim 1, wherein said process further comprises the step of contacting said marine organism skeletal derivative-based solid material with a fluid and applying negative pressure to said marine organism skeletal derivative-based solid material allowing for maximal uptake of said fluid within said marine organism skeletal derivative-based solid material to arrive at said total fluid uptake value.

8. The process of claim 1, wherein said specific fluid uptake capacity value is a function of change in weight in said marine organism derivative-based solid material or wherein said specific fluid uptake capacity value is a function of change in fluid volume of applied fluid to said marine organism skeletal derivative-based solid material.

9. The process of claim 1, wherein said biologic fluid is autologous with respect to a cell or tissue of a subject when said solid substrate is contacted with a cell or tissue of said subject.

10. The process of claim 1, wherein said fluid used to establish the specific fluid update capacity value is water, plasma or blood.

11. The process of claim 1, wherein said marine organism skeletal derivative-based solid material approximates the form of a cylinder, cone, tac, pin, screw, rectangular bar, plate, disc, pyramid, granule, ball, valve, prosthesis, coating for a prosthesis, stent or cube or wherein said marine organism skeletal derivative-based solid material approximates a shape that accommodates a site of desired mitigation of cell or tissue adhesion.

12. The process of claim 2, wherein said marine organism skeletal derivative-based solid material comprises a hollow or hollows along a Cartesian coordinate axis of said coral or coral-based derivative or of said aragonite, calcite, hydroxyapatite or combination thereof.

13. The process of claim 1, wherein said marine organism skeletal derivative-based solid material comprises a biocompatible polymer.

14. The process of claim 13, wherein said biocompatible polymer is incorporated within voids or pores in said substrate or wherein said biocompatible polymer is attached to an outer surface of said substrate.

15. The process of claim 13, wherein said biocompatible polymer comprises a natural polymer comprising a glycosaminoglycan, collagen, fibrin, elastin, silk, chitosan, alginate, and any combinations thereof.

16. The process of claim 15, wherein said glycosaminoglycan is hyaluronic acid, sodium hyaluronate, cross linked hyaluronic acid, or a combination thereof.

17. The process of claim 1, wherein said marine organism skeletal derivative-based solid material further comprises a cytokine, a growth factor, a therapeutic compound, a drug, metal ion, metal hydride, metal oxide or any combination thereof, wherein said therapeutic compound or drug comprises an anti-inflammatory compound, an anti-infective compound, a pro-angiogenic factor or a combination thereof.

18. The process of claim 1, wherein said solid substrate is useful in preventing undesired vascularization at a site of implantation of said solid substrate; or wherein said solid substrate is useful in reducing the incidence or severity of, or treating neoplasia, macular degeneration, hemangioma, diabetic retinopathy, arthritis, psoriasis, ocular neovascular disease, tumor formation and metastasis in tumors, ulcerative colitis, Crohn's disease, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eales' disease, Bechet's disease, infections causing a retinitis or choroiditis, presumed ocular histoplasmosis, Best's disease, myopia, optic pits, Stargardt's disease, pars planitis, chronic retinal detachment, hyperviscosity syndromes, and toxoplasmosis; or wherein said solid substrate is useful in preventing graft versus host disease or host versus graft disease; or wherein said solid substrate is useful in promoting release of a therapeutic material over time located within said solid substrate and formulated for release from therewithin; or wherein said solid substrate is useful in promoting release of a therapeutic material over time located within said solid substrate and formulated for release from therewithin; or wherein said solid substrate is useful in treating a neurodegenerative disease; or wherein said solid substrate is useful as a surface coating for synovial shunts, stents or valves; or wherein said solid substrate is useful as a covering material for prevention or mitigation of tissue/cell growth on a surface located substantially underneath such covering; or wherein said solid substrate is useful as a substrate for in vitro cell and tissue growth whose growth is promoted by contact independence; or wherein said solid substrate is useful as a substrate for in vitro cell and tissue growth of cells and tissue of neuronal origin.

19. A solid substrate for mitigating or preventing cell or tissue adhesion and vascularization, which solid substrate is selected by the process of claim 1.

20. A kit comprising at least one solid substrate of claim 19.

* * * * *